(12) United States Patent
Mossakowska et al.

(10) Patent No.: US 6,833,437 B2
(45) Date of Patent: Dec. 21, 2004

(54) COMPLEMENT RECEPTOR TYPE 1 (CR1)-LIKE SEQUENCES

(75) Inventors: Danuta Ewa Irena Mossakowska, Essex (GB); Vivienne Frances Cox, Herts (GB); Richard Anthony Godwin Smith, Herts (GB)

(73) Assignee: AdProTech Limited, Essex (GB)

( * ) Notice: Subject to any disclaimer, the term of this patent is extended or adjusted under 35 U.S.C. 154(b) by 0 days.

(21) Appl. No.: 09/380,682

(22) PCT Filed: Mar. 5, 1998

(86) PCT No.: PCT/GB98/00727

§ 371 (c)(1),
(2), (4) Date: Oct. 19, 1999

(87) PCT Pub. No.: WO98/39433

PCT Pub. Date: Sep. 11, 1998

(65) Prior Publication Data

US 2003/0064431 A1 Apr. 3, 2003

(30) Foreign Application Priority Data

Mar. 5, 1997 (GB) .............................. 9704519

(51) Int. Cl.⁷ .......................... C07K 1/00; C07H 21/04; C12N 1/20; C12P 21/06; G01N 33/567
(52) U.S. Cl. .......................... 530/350; 435/6; 435/7.21; 435/69.1; 435/252.3; 435/320.1; 436/501; 514/2; 530/402; 536/23.5
(58) Field of Search .............................. 514/2; 530/350, 530/402; 435/69.1, 252.3, 6, 7.21, 320.1; 536/23.5; 436/501

(56) References Cited

U.S. PATENT DOCUMENTS 5,545,619 A * 8/1996 Atkinson et al. ............. 514/12
5,936,092 A * 8/1999 Shen et al. .................. 546/294

FOREIGN PATENT DOCUMENTS

| EP | 0512733 A2 | 11/1992 |
|---|---|---|
| WO | WO94/00571 | 1/1994 |
| WO | WO95/08343 | 3/1995 |
| WO | WO98/02454 | 1/1998 |

OTHER PUBLICATIONS

Hourcade et al., J. Biol. Chem. 265(2)974–980, Jan. 1990.*
Clissold, et al., Eur. J. Immunology 23:2346–2352, 1993.*
Coyne et al., Journal of Immunology 149: 2906–2913 (1992).
Hourcade et al., Journal of Biological Chemistry 265(2): 974–980 (1990).
Makrides et al., Journal of Biological Chemistry 267(34): 24754–24761 (1992).

* cited by examiner

Primary Examiner—Lorraine Spector
Assistant Examiner—Michael Brannock
(74) Attorney, Agent, or Firm—Heller Ehrman White & McAuliffe

(57) ABSTRACT

Replacement of codons in DNA encoding the first three SCRs of LHR-A of CR1 with others encoding the predicted amino acids in the CR1-like sequence can give rise to chimeric genes which can be expressed to give active complement inhibitors with functional complement inhibitory, including anti-haemolytic activity. There is provided a soluble polypeptide comprising, in sequence, one to four short consensus repeats (SCR) selected from SCR 1, 2, 3 and 4 of long homologous repeat A (LHR-A) as the only structurally and functionally intact SCR domains of CR1 and including at least SCR3, in which one or more of the native amino acids are substituted with the following: Val 4, Asp 19, Scr 53, Lys 57, Ala 74, Asp 79, Arg 84, Pro 91, Asn 109, Lys 116, Val 119, Ala 132, Thr 137, Ile 139, Ser 140, Tyr 143, His 153, Leu 156, Arg 159, Lys 161, Lys 177, Gly 230, Ser 235, His 236.

2 Claims, No Drawings

COMPLEMENT RECEPTOR TYPE 1 (CR1)-LIKE SEQUENCES

This invention relates to novel polypeptides and their derivatives which act as inhibitors or regulators of complement activation and are of use in the therapy of diseases involving complement activation such as various inflammatory and immune disorders.

Constituting about 10% of the globulins in normal serum, the complement system is composed of many different proteins that are important in the immune system's response to foreign antigens. The complement system becomes activated when its primary components are cleaved and the products alone or with other proteins, activate additional complement proteins resulting in a proteolytic cascade. Activation of the complement system leads to a variety of responses including increased vascular permeability, chemotaxis of phagocytic cells, activation of inflammatory cells, opsonization of foreign particles, direct killing of cells and tissue damage. Activation of the complement system may be triggered by antigen-antibody complexes (the classical pathway) or, for example, by lipopolysaccharides present in cell walls of pathogenic bacteria (the alternative pathway).

Complement activation (CA) is known to occur in a wide variety of acute inflammatory processes particularly those associated with ischaemia and reperfusion injury (Rossen et al., 1985 Circ. Res., 57, 119,; Morgan B. P., 1990 The biological effects of complement activation. In 'Complement, Clinical Aspects and Relevance to Disease'. Academic Press. London.)

It is also generally accepted that at least some of the components of the classical complement cascade can be detected by immunohistochemical methods in close association with senile plaques in the brains of sufferers from Alzheimer's disease (Eikelenboom et al., 1994, Neuroscience, 59, 561–568) and that complement activation plays a role in the inflammatory component of this condition.

Complement receptor type 1 (CR1) has been shown to be present on the membranes of erythrocytes, monocytes/macrophages, granulocytes, B cells, some T cells, splenic follicular dendritic cells, and glomerular podocytes. CR1 binds to the complement components C3b and C4b and has also been referred to as the C3b/C4b receptor. The structural organisation and primary sequence of one allotype of CR1 is known (Klickstein et al., 1987, J. Exp. Med. 165:1095–1112, Klickstein et al., 1988, J. Exp. Med. 168:1699–1717; Hourcade et al., 1988, J. Exp. Med. 168:1255–1270, WO 89/09220, WO 91/05047). It is composed of 30 short consensus repeats (SCRs) that each contain around 60–70 amino acids. In each SCR, around 29 of the average 65 amino acids are conserved. Each SCR has been proposed to form a three dimensional triple loop structure through disulphide linkages with the third and first and the fourth and second half-cystines in disulphide bonds. CR1 is further arranged as 4 long homologous repeats (LHRs) of 7 SCRs each. Following a leader sequence, the CR1 molecule consists of the N-terminal LHR-A, the next two repeats, LHR-B and LHR-C, and the most C-terminal LHR-D followed by 2 additional SCRs, a 25 residue putative transmembrane region and a 43 residue cytoplasmic tail.

Based on the mature CR1 molecule having a predicted N-terminal glutamine residue, hereinafter designated as residue 1, the first four SCR domains of LHR-A are defined herein as consisting of residues 2–58, 63–120, 125–191 and 197–252, respectively, of mature CR1.

Hourcade et al., 1988, J. Exp. Med. 168:1255–1270 observed an alternative polyadenylation site in the human CR1 transcriptional unit that was predicted to produce a secreted form of CR1. The mRNA encoded by this truncated sequence comprises the first 8.5 SCRs of CR1, and encodes a protein of about 80 kDa which was proposed to include the C4b binding domain. When a cDNA corresponding to this truncated sequence was transfected into COS cells and expressed, it demonstrated the expected C4b binding activity but did not bind to C3b (Krych et al., 1989, FASEB J. 3:A368; Krych et al. Proc. Nat. Acad. Sci. 1991, 88, 4353–7). Krych et al., also observed a mRNA similar to the predicted one in several human cell lines and postulated that such a truncated soluble form of CR1 with C4b binding activity may be synthesised in humans.

In addition, Makrides et al. (1992, J. Biol. Chem. 267 (34) 24754–61) have expressed SCR 1+2 and 1+2+3+4 of LHR-A as membrane-attached proteins in CHO cells.

Several soluble fragments of CR1 have also been generated via recombinant DNA procedures by eliminating the transmembrane region from the DNAs being expressed (WO 89/09220, WO 91/05047). The soluble CR1 fragments were functionally active, bound C3b and/or C4b and demonstrated Factor I cofactor activity depending upon the regions they contained. Such constructs inhibited in vitro complement-related functions such as neutrophil oxidative burst, complement mediated hemolysis, and C3a and C5a production. A particular soluble construct, sCR1/pBSCR1c, also demonstrated in vivo activity in a reversed passive Arthus reaction (WO 89/09220, WO 91/05047; Yeh et al., 1991, J. Immunol. 146:250), suppressed post-ischemic myocardial inflammation and necrosis (WO 89/09220, WO 91/05047; Weisman et al., Science, 1990, 249:146–1511, Dupe, R. et al. Thrombosis & Haemostasis (1991) 65(6) 695.) and extended survival rates following transplantation (Pruitt & Bollinger, 1991, J. Surg. Res 50:350; Pruitt et al., 1991 Transplantation 52; 868). Furthermore, co-formulation of sCR1/pBSCR1c with p-anisoylated human plasminogen-streptokinase-activator complex (APSAC) resulted in similar anti-haemolytic activity as sCR1 alone, indicating that the combination of the complement inhibitor sCR1 with a thrombolytic agent was feasible (WO 91/05047).

In a model of antibody-mediated demyelinating experimental allergic encephalomyclitis (ADEAE), systemic inhibition of CA using sCR1 over 6 days, produced improvements in clinical score and blocked CNS inflammation, demyelination and deposition of complement components (Piddlesden et al., 1994, J. Immunol. 152, 5477). ADEAE can be regarded as a model of acute relapse in multiple sclerosis (MS) and these striking results suggested possible applications for sCR1 in MS therapy despite the high molecular weight (245 kilodaltons) of this agent.

In a rat model of traumatic brain injury, complement inhibitor sCR1 (also known as TP10 or BRL55730) was shown to reduce myeloperoxidase activity (an indicator of neutrophil accumulation) following traumatic injury (Kaczorowska et al, 1995, J. Cerebral Blood Flow and Metabolism, 15, 860–864). This is suggested as demonstrating that complement activation is involved in the local inflammatory response.

Soluble polypeptides corresponding to part of CR1 having functional complement inhibitory, including anti-haemolytic activity, have been described in WO94/00571 comprising, in sequence, one to four short consensus repeats (SCR) selected from SCR 1, 2, 3 and 4 of long homologous repeat A (LHR-A) as the only structurally and functionally intact SCR domains of CR1 and including at least SCR3.

Pseudogenes are usually defined as DNA sequences which possess a high degree of homology to genes with identified function but which are not expressed. The origins of the lack of transcription and translation vary but are commonly the presence of accumulated mutations which inactivate inscriptional initiation sites, disrupt RNA splicing or introduce frame-shift mutations and premature termination codons. Pseudogenes are sometimes regarded as genetic relics which have been isolated within the genome through a primary loss of expressability and which have subsequently mutated randomly in situ to highly aberrant forms. There is a frequent presumption that pseudogene sequences, if expressable at all, will not be functionally active because of an accumulation of deleterious in-frame mutations. However, studies of immune system genetics suggest that pseudogenes may act as a source of diversity in somatic mutation processes and that non-expressed sequences may recombine with normally expressed genes to create functional variants with a conserved framework. This phenomenon has been documented in immunoglobulin VL and VH genes and elsewhere (W. T. McCormack et al., Genes Dev. 4, 548–58, 1990).

The creation of pseudogenes through reverse transcription followed by DNA integration is also known. In such cases, the integrated sequences (which can in principle originate from organisms other than the host) lack introns and may be sited in chromosomal locations distant from the expressed gene to which they are homologous because integration into the genome can occur at random sites. Such genes are known as processed pseudogenes. The presence of pseudogenes in chromosomal clusters with homologous expressed genes argues against them being processed pseudogenes because of the improbability of a random integration process giving rise to close physical clustering in a large genome.

The existence of a gene homologous to that for complement receptor type 1 (CR1) was first reported by Hourcade et al. (J.Biol.Chem, 275, 974–80, 1990), who found it associated with a gene cluster on chromosome 1q 32 termed the Regulators of Complement Activation (RCA) cluster. The latter comprises the CR1 gene itself and those encoding decay accelerating factor (DAF), membrane cofactor protein (MCP), Factor H, complement receptor type 2 (CR2) and C4 binding protein. This 'CR1-like' gene was predicted to encode a protein containing seven SCR regions corresponding (by closest homology) to SCRs 1–6 and 9 of LHR-A (1–6) or LHR-B (9) of CR1 itself. The overall homology with the above regions of CR1 at the predicted amino acid level is 91% and the sequence divergence is greatest in the first three SCRs.

```
        ALIGNMENT OF CR1-LIKE GENE (Cr1pse) (SEQ ID NO:58) WITH
        THE HUMAN CR1 SEQUENCE (Cr1.Pe, LHRA region) (SEQ ID NO:59)
              (NB. CR1 numbering includes the signal sequence)
                       80.7% identity in 446 aa overlap 10        20        30
Cr1pse                                  QCVVPEWLPFARPTNLTDDFEFPIGTYLNY
                                        |||:||||||||||||||:||||||||||||
Cr1.Pe  VGPPAPGLPFCCGGSLLAVVVLLALPVAWGQCVAPEWLPFARPTNLTDEFEFPIGTYLNY
           20        30        40        50        60        70

40        50        60        70        80        90
Cr1pse  ECRPGYSGRPFSIICLKNSVWTSAKDKCKRKSCRNPPDPVNGMAHVIKDIQFRSQIKYSC
        ||||||||||||||||||||||:|||:|:|||||||||||||||:||||:||| ||||||
Cr1.Pe  ECRPGYSGRPFSIICLKNSVWTGAKDRCRRKSCRNPPDPVNGMVHVIKGIQFGSQIKYSC
           80        90       100       110       120       130

100       110       120       130       140       150
Cr1pse  PKGYRLIGSSSATCIISGNTVIWDNKTPVCDRIICGLPPTIANGDFTSISREYFHYGSVV
        :|||||||||||||||:||||||:||:||||  ||||||:||||:|:|::|| ||||||
Cr1.Pe  TKGYRLIGSSSATCIISGDTVIWDNETPICDRIPCGLPPTITNGDFISTNRENFHYGSVV
          140       150       160       170       180       190

160       170       180       190       200       210
Cr1pse  TYHCNLGSRGKKVFELVGEPSIYCTSKDDQVGIWSGPAPQCIIPNKCTPPNVENGILVSD
        ||:||  ||  |:|||||||||||||:|||||||||||||||||||||||||||||||
Cr1.Pe  TYRCNPGSGGRKVFELVGEPSIYCTSNDDQVGIWSGPAPQCIIPNKCTPPNVENGILVSD
          200       210       220       230       240       250

220       230       240       250       260       270
Cr1pse  NRSLFSLNEVVEFRCQPGFGMKGPSHVKCQALNKWEPELPSCSRVCQPPPDVLHAERTQR
        ||||||||||||||||||||  ||::||||||||||||||||||||||||||||||||||
Cr1.Pe  NRSLFSLNEVVEFRCQPGFVMKGPRRVKCQALNKWEPELPSCSRVCQPPPDVLHAERTQR
          260       270       280       290       300       310

280       290       300       310       320       330
Cr1pse  DKDNFSPGQEVFYSCEPGYDLRGSTYLHCTPQGDWSPAAPRCEVKSCDDFLGQLPNGHVL
        ||||||||||||||||||||||||::  ::|||||||||||| |||||||||:|||:||
Cr1.Pe  DKDNFSPGQEVFYSCEPGYDLRGAASMRCTPQGDWSPAAPTCEVKSCDDFMGQLLNGRVL
          320       330       340       350       360       370

340       350       360       370       380       390
Cr1pse  FPLNLQLGAKVDFVCDEGFQLKGSSASYCVLAGMESLWNSSVPVCERESCKTPPVPVNGM
        ||:||||||||||||||||||||||||||||||||||||||||||||: | :||| ||:
Cr1.Pe  FPVNLQLGAKVDFVCDEGFQLKGSSASYCVLAGMESLWNSSVPVCEQIFCPSPPVIPNGR
          380       390       400       410       420       430
```

-continued

ALIGNMENT OF CR1-LIKE GENE (Cr1pse) (SEQ ID NO:58) WITH
THE HUMAN CR1 SEQUENCE (Cr1.Pe, LHRA region) (SEQ ID NO:59)
(NB. CR1 numbering includes the signal sequence)
80.7% identity in 446 aa overlap

```
            400           410       420        430
Cr1pse --VHVITDIHVGSRINYSC------TTGHRLIGHSSAECIL-SGNTAHWSMKPPICQ
         : :: ::  |: :||:|      :|:  |||:|:  |:  : :::  ||  :| |
Cr1.Pe HTGKPLEVFPFGKAVNYTCDPHPDRGTSFDLIGESTIRCTSDPQGNGVWSSPAPRCG
          440         450       460       470       480       490
```

The CR1-like gene also encodes a signal peptide but not a transmembrane or cytoplasmic region and contains an intron-exon structure similar to the CR1 gene. There is currently no evidence that the CR1-like gene is expressed and neither mRNA transcripts nor a soluble protein have been isolated. The origin of the CR1-like sequence may lie in a gene duplication event in an ancestral CR1 gene which was followed by divergence and transcriptional inactivation of the CR1-like gene. It appears probable that the CR1-like gene is currently a pseudogene although not of the processed type.

It has now been found that replacement of codons in DNA encoding the first three SCRs of LHR-A of CR1 with others encoding the predicted aminoacids in the CR1-like sequence can give rise to chimeric genes which can be expressed to give active complement inhibitors with functional complement inhibitory, including anti-haemolytic, activity.

According to the present invention there is provided a soluble polypeptide comprising, in sequence, one to four short consensus repeats (SCR) selected from SCR 1, 2, 3 and 4 of long homologous repeat A (LHR-A) as the only structurally and functionally intact SCR domains of CR1 and including at least SCR3, in which one or more of the native amino acids are substituted with the following:

Val 4, Asp 19, Ser 53, Lys 57, Ala 74, Asp 79, Arg 84, Pro 91, Asn 109, Lys 116, Val 119, Ala 132, Thr 137, Ile 139, Ser 140, Tyr 143, His 153, Leu 156, Arg 159, Lys 161, Lys 177, Gly 230, Ser 235, His 236.

(Numbering is from glutamine as residue 1 of mature CR1. The amino-acid indicated is that which replaces the CR1 residue at the position specified.).

In preferred aspects, the polypeptide comprises, in sequence, SCR 1, 2, 3 and 4 of LHR-A or SCR 1, 2 and 3 of LHR-A as the only structurally and functionally intact SCR domains of CR1 with the modification(s) described above.

It is to be understood that additional variations in the amino acid sequence of the polypeptide of the invention by way of addition, deletion or conservative substitution of residues, including allelic variations, in which the biological activity of the polypeptide is retained, are encompassed by the invention. Conservative substitution is understood to mean the retention of the charge and/or size characteristics of the amino acid side chain, for example arginine replaced by lysine or glutamine.

In one aspect, the polypeptide of the invention may be represented symbolically as follows:

$$NH_2-V^1-SCR1-W^1-SCR2-X^1-SCR3-Y^1-OH \qquad (I)$$

in which SCR1 represents residues 2–58 of mature CR1, SCR2 represents residues 63–120 of mature CR1, SCR3 represents residues 125–191 of mature CR1, and containing at least one of the substitutions as aforesaid and $V^1$, $W^1$, and $Y^1$ represent bonds or short linking sequences of amino acids, preferably 1 to 5 residues in length and which are preferably derived from native interdomain sequences in CR1.

The native interdomain sequences in CR1 may also be substituted with the corresponding predicted aminoacids in the CR1-like sequence, namely Lys59 and/or Ile124. (Numbering is from glutamine as residue 1 of mature CR1. The amino-acid indicated is that which replaces the CR1 residue at the position specified.)

In a preferred embodiment, the SCR3 domain of formula (I) is substituted with all ten residues found in the corresponding pseudogene sequence, namely (in single letter code):

A132, T137, I139, S140, Y143, H153, L156,
R159, K161, K177 (Sequence Group 1)

and the remaining domains have the sequence of mature CRI.

In a further preferred embodiment of formula (I), $W^1$, $X^1$ and $Y^1$ represent residues 59–62, 121–124 and 192–196, respectively, of mature CR1, optionally substituted as aforesaid and $V^1$ represents residue 1 of mature CR1 optionally linked via its N-terminus to methionine.

In another aspect the polypeptide of the invention may be represented symbolically as follows:

$$NH_2-V^2-SCR1-W^2-SCR2-X^2-SCR3-Y^2-SCR4-Z^2OH \qquad (II)$$

in which SCR1, SCR2 and SCR3 are as hereinbefore defined, SCR4 represents residues 197–252 of mature CR1 and containing at least one of the substitutions as aforesaid, and $V^2$, $W^2$, $X^2$, $Y^2$ and $Z^2$ represent bonds or short linking sequences of amino acids, preferably 1 to 5 residues in length and which are preferably derived from native interdomain sequences in CR1, optionally substituted as aforesaid.

In a preferred embodiment of formula (II)), the SCR3 region is substituted with the aforementioned Sequence Group 1 residues and the remaining domainshave the sequence of mature CR1.

In further preferred embodiments of formula (II), $W^2$, $X^2$, $Y^2$ and $Z^2$ represent residues 59–62, 121–124, 192–196, and residues 253 respectively, of mature CR1, optionally substituted as aforesaid, and $V^2$ represents residue 1 of mature CR1 optionally linked via its N-terminus to methionine.

In one particular embodiment of formula (II) arginine 235 is replaced by histidine.

In the preferred embodiment of formula (II), residue 235 is arginine.

In one further aspect, the polypeptide of the invention may be represented symbolically as follows:

$$NH_2-X^3-SCR3-Y^3-OH \qquad (III)$$

in which SCR3 is as hereinbefore defined, containing at least one of the substitutions as aforesaid, and in a preferred embodiment, all those of Sequence Group 1, and $X^3$ and $Y^3$ represent bonds or short linking sequences of amino acids, preferably 1 to 5 residues in length and which are preferably derived from native interdomain sequences in CR1, optionally substituted as aforesaid.

In a further preferred embodiment of formula (III) $X^3$ represents amino acids 122–124 of mature CR1, optionally substituted as aforesaid, optionally linked to methionine at its N-terminus and $Y^4$ represents amino acids 192–196 of mature CR1.

In another further aspect, the polypeptide of the invention may be represented symbolically as follows:

$$NH_2\text{-}X^4\text{-}SCR3\text{-}Y^4\text{-}SCR4\text{-}Z^4\text{-}OH \quad (IV)$$

in which SCR3 and SCR4 are as hereinbefore defined containing at least one of the substitutions as aforesaid and $X^4$, $Y^4$ and $Z^4$ represent bonds or short linking sequences of amino acids, preferably 1 to 5 residues in length and which are preferably derived from native interdomain sequences in CR1, optionally substituted as aforesaid.

In a preferred embodiment of formula (IV), the SCR3 region is substituted with the residues of Sequence Group 1 and the remaining domainshave the sequence of mature CR1.

In a further preferred embodiment of formula (IV) $X^4$ represents amino acids 122–124 of mature CR1, optionally substituted as aforesaid, optionally linked to methionine at its N-terminus and $Y^4$ and $Z^4$ represent amino acids 192–196 and 253 respectively of mature CR1.

The soluble polypeptides of the invention lack the membrane binding capability of the full length CR1 proteins which properties may be advantageous to the therapeutic activity.

The main classes of interaction of proteins with membranes can be summarised as follows:

1. Direct and specific interactions with phospholipid head groups or with other hydrophilic regions of complex lipids or indirectly with proteins already inserted in the membrane. The latter may include all the types of intrinsic membrane protein noted below and such interactions are usually with extracellular domains or sequence loops of the membrane proteins;

2. Through anchoring by a single hydrophobic transmembrane helical region near the terminus of the protein. These regions commonly present a hydrophobic face around the entire circumference of the helix cylinder and transfer of this structure to the hydrophilic environment of bulk water is energetically unfavourable.

3. Further anchoring is often provided by a short sequence of generally cationic aminoacids at the cytoplasmic side of the membrane, C-terminal to the transmembrane helix. The membrane-binding properties or CR1 are provided by features 2 and 3.

4. Through the use of multiple (normally 2–12 and commonly 4, 7 and 10) transmembrane regions which are usually predicted to be helical or near-helical. Although these regions are normally hydrophobic overall, they frequently show some amphipathic behaviour—an outer hydrophobic face and an inner more hydrophilic one being identifiable within a helix bundle located in the lipid bilayer;

5. Through postranslationally linked phosphatidyl inositol moieties (GPI-anchors). These are generated by a specific biosynthetic pathway which recognises and removes a specific stretch of C-terminal aminoacids and creates a membrane-associating diacyl glycerol unit linked via a hydrophilic carbohydrate spacer to the polypeptide;

6. In a related process, single fatty acid groups such as myristoyl, palmitoyl or prenyl may be attached postranslationally to one or more sites in a protein (usually at N- or C-termini). Again, amino acids (such as the C-terminal CAAX box in Ras proteins) may be removed.

The present invention further provides a soluble derivative of the soluble polypeptide of the invention, said derivative comprising two or more heterologous membrane binding elements with low membrane affinity covalently associated with the polypeptide which elements are capable of interacting independently and with thermodynamic additivity with components of cellular membranes exposed to extracellular fluids.

By 'heterologous' is meant that the elements are not found in the native full length CR1 protein.

By 'membrane binding element with low membrane affinity' is meant that the element has significant affinity for membranes, that is a dissociation constant greater than 1 $\mu$M, preferably 1 $\mu$M–1 mM. The elements preferably have a size <5 kDa.

The derivative should incorporate sufficient elements with low affinities for membrane components to result in a derivative with a high (preferably 0.01–10 nM dissociation constant) affinity for specific membranes. The elements combine so as to create an overall high affinity for the particular target membrane but the combination lacks such high affinity for other proteins for which single elements may be (low-affinity) ligands.

The elements should be chosen so as to retain useful solubility in pharmaceutial formulation media, preferably >100 $\mu$g/ml. Preferably at least one element is hydrophilic.

The further embodiment of the invention thus promotes localisation of the polypeptide of the invention at cellular membranes and thereby provide one or more of several biologically significant effects with potential therapeutic advantages including:

Potency: an increase in effective concentration may result from the reduction in the diffusional degrees of freedom.

Pharmacokinetics and dosing frequency: Interaction of the derivatised polypeptide with long-lived cell types or serum proteins would be expected to prolong the plasma residence time of the polypeptide and produce a depot effect through deposition on cell surfaces.

Specificity: Many clinically important pathological processes are associated with specific cell types and tissues (for example the vascular endothelium and the recruitment thereto of neutrophils bearing the sialyl Lewis$^x$ antigen to ELAM-1, see below). Hence targeting the modified polypeptide to regions of membrane containing pathology-associated membrane markers may improve the therapeutic ratio of the protein targeted.

It will be appreciated that all associations of heterologous amino acid sequences with the polypeptide will need to be assessed for potential immunogenicity, particularly where the amino acid sequence is not derived from a human protein. The problem can be minimised by using sequences as close as possible to known human ones and through computation of secondary structure and antigenicity indices.

The derivative preferably comprises two to eight, more preferably two to four membrane binding elements.

Membrane binding elements are preferably selected from: fatty acid derivatives such as fatty acyl groups; basic amino acid sequences; ligands of known integral membrane proteins; sequences derived from the complementarity-determining region of monoclonal antibodies raised against epitopes of membrane proteins; membrane binding sequences identified through screening of random chemical libraries.

The selection of suitable combination of membrane binding elements will be guided by the nature of the target cell membrane or components thereof.

Suitable fatty acid derivatives include myristoyl (12 methylene units) which is insufficiently large or hydrophobic to permit high affinity binding to membranes. Studies with myristoylated peptides (eg R. M. Peitzsch & S. McLaughlin, Biochemistry, 32, 10436–10443, 1993)) have shown that they have effective dissociation constants with model lipid systems of ~$10^{-4}$ M and around 10 of the 12 methylene groups are buried in the lipid bilayer. Thus, aliphatic acyl groups with between about 8 and 18 methylene units, preferably 10–14, are suitable membrane binding elements. Other examples of suitable fatty acid derivatives include long-chain (8–18, preferably 10–14 methylene) aliphatic amines and thiols, steroid and farnesyl derivatives.

Membrane binding has been found to be associated with limited (single-site) modification with fatty acyl groups when combined with a cluster of basic aminoacids in the protein sequence which may interact with acidic phospholipid head groups and provide the additional energy to target membrane binding. This combination of effects has been termed the 'myrstoyl-electrostatic switch' (S. McLaughlin and A. Aderem, TIBS, 20,272–276, 1994; J. F. Hancock et al, Cell, 63, 133–139,1990). Thus, a further example of suitable membrane binding elements are basic aminoacid sequences such as those found in proteins such as Ras and MARCKS (myristoylated alanine-rich C-kinase substrate, P. J. Blackshear, J. Biol. Chem., 268, 1501–1504, 1993) which mediate the electrostatic 'switch' through reversible phosphorylation of serine residues within the sequence and a concomitant neutralisation of the net positive charge. Such sequences include but are not restricted to consecutive sequences of Lysine and Arginine such as (Lys)n where n is between 3 and 10, preferable 4 to 7.

Suitable examples of amino acid sequences (SEQ ID NOS 60, 61, & 62 respectively) comprising basic amino acids include:

DGPKKKKKKSPSKSSG            i)

GSSKSPSKKKKKKPGD            ii)

SPSNETPKKKKKRFSFKKSG      iii)

(N-terminus on left)
Sequences i) to iii) are examples of electrostatic switch sequences.

Examples of amino acid sequences include RGD-containing peptides such as GRGDSP (SEQ ID NO:63) which are ligands for the $\alpha_{IIb}\beta_3$ integrin of human platelet membranes. Further examples of such sequences include those known to be involved in interactions between membrane proteins such as receptors and the major histocompatibility complex. An example of such a membrane protein ligand is the sequence (SEQ ID NO:64) GNEQSFRVDL-RTLLRYA which has been shown to bind to the major histocompatibility complex class 1 protein (MHC-1) with moderate affinity (L. Olsson et al, Proc. Natl. Acad.Sci.USA. 91, 9086–909, 1994).

An example of a ligand for an integral membrane protein is the carbohydrate ligand Sialyl Lewis$^x$ which has been identified as a ligand for the integral membrane protein ELAM-1 (M. L. Phillips et al, Science, 250, 1130–1132, 1990 & G. Walz et al, Ibid. 250, 1132–1135,1990).

Sequences derived from the complementarity-determining regions of monoclonal antibodies raised against epitopes within membrane proteins (see, for example, J. W. Smith et al, J.Biol.Chem. 270, 30486–30490, 1995) are also suitable membrane binding elements, as are binding sequences from random chemical libraries such as those generated in a phage display format and selected by bio-panning operations in vitro (G. F. Smith and J. K. Scott, Methods in Enzymology, 217H, 228–257,1993) or in vivo (R. Pasqualini & E. Ruoslahti, Nature, 380, 364–366, 1996).

Optionally, conditional dissociation from the membrane may be incorporated into derivatives of the invention using mechanisms such as pH sensitivity (electrostatic switches), regulation through metal ion binding (using endogenous $Ca^{2+}$, $Z^{2+}$ and incorporation of ion binding sites in membrane binding elements) and protease cleavage (e.g plasminolysis of lysine-rich membrane binding sequences to release and activate prourokinase)

Preferred derivatives of this invention have the following structure:

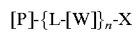

in which:

P is the soluble polypeptide, each L is independently a flexible tinker group, each W is independently a peptide membrane binding element, n is an integer of 1 or more and X is a peptide or non-peptide membrane-binding entity which may be covalently linked to any W.

Peptide membrane binding elements are preferably located sequentially either at the N or C terminus of the soluble polypeptide and are preferably 8 to 20 amino acids long. The amino acid sequences are linked to one another and to the soluble peptide by linker groups which are preferably selected from hydrophilic and/or flexible aminoacid sequences of 4 to 20 aminoacids; linear hydrophilic synthetic polymers; and chemical bridging groups.

In a further aspect, the invention provides a process for preparing a polypeptide according to the invention which process comprises expressing DNA encoding said polypeptide in a recombinant host cell and recovering the product.

In particular, the process may comprise the steps of:
i) preparing a replicable expression vector capable, in a host cell, of expressing a DNA polymer comprising a nucleotide sequence that encodes said polypeptide;
ii) transforming a host cell with said vector;
iii) culturing said transformed host cell under conditions permitting expression of said DNA polymer to produce said polypeptide; and
iv) recovering said polypeptide.

The DNA polymer comprising a nucleotide sequence that encodes the polypeptide also forms part of the invention.

The process of the invention may be performed by conventional recombinant techniques such as described in Sambrook et al., Molecular Cloning: A laboratory manual 2nd Edition. Cold Spring Harbor Laboratory Press (1989) and DNA Cloning vols I, II and III (D. M. Glover ed., IRL Press Ltd).

The invention also provides a process for preparing the DNA polymer by the condensation of appropriate mono-, di- or oligomeric nucleotide units.

The preparation may be carried out chemically, enzymatically, or by a combination of the two methods, in vitro or in vivo as appropriate. Thus, the DNA polymer may be prepared by the enzymatic ligation of appropriate DNA fragments, by conventional methods such as those described by D. M. Roberts et al., in Biochemistry 1985, 24, 5090–5098.

The DNA fragments may be obtained by digestion of DNA containing the required sequences of nucleotides with appropriate restriction enzymes, by chemical synthesis, by enzymatic polymerisation, or by a combination of these methods.

Digestion with restriction enzymes may be performed in an appropriate buffer at a temperature of 20°–70° C., generally in a volume of 50 µl or less with 0.1–10 µg DNA.

Enzymatic polymerisation of DNA may be carried out in vitro using a DNA polymerase such as DNA polymerase 1 (Klenow fragment) in an appropriate buffer containing the nucleoside triphosphates dATP, dCTP, dGTP and dTTP as required at a temperature of 10°–37° C., generally in a volume of 50 µl or less.

Enzymatic ligation of DNA fragments may be carried out using a DNA ligase such as T4 DNA ligase in an appropriate buffer at a temperature of 4° C. to 37° C., generally in a volume of 50 µl or less.

The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory Manual' (ed. H. G. Gassen and A. Lang), Verlag Chemie, Weinheim (1982), or in other scientific publications, for example M. J. Gait, H. W. D. Matthes M. Singh, B. S. Sproat and R. C. Titmas, Nucleic Acids Research, 1982, 10, 6243; B. S. Sproat and W. Banawarth, Tetrahedron Letters, 1983, 24, 5771; M. D. Matteucci and M. H. Caruthers, Tetrahedron Letters, 1980, 21, 719; M. D. Matteucci and M. H. Caruthers, Journal of the American Chemical Society, 1981, 103, 3185; S. P. Adams et al., Journal of the American Chemical Society, 1983, 105, 661; N. D. Sinha, J. Biernat, J. McMannus and H. Koester, Nucleic Acids Research, 1984, 12, 4539; and H. W. D. Matthes et al., EMBO Journal, 1984, 3, 801. Preferably an automated DNA synthesiser (for example, Applied Biosystems 381A Synthesiser) is employed.

The DNA polymer is preferably prepared by ligating two or more DNA molecules which together comprise a DNA sequence encoding the polypeptide.

The DNA molecules may be obtained by the digestion with suitable restriction enzymes of vectors carrying the required coding sequences.

The precise structure of the DNA molecules and the way in which they are obtained depends upon the structure of the desired product. The design of a suitable strategy for the construction of the DNA molecule coding for the polypeptide is a routine matter for the skilled worker in the art.

In particular, consideration may be given to the codon usage of the particular host cell. The codons may be optimised for high level expression in $E.$ $coli$ using the principles set out in Devereux et al., (1984) Nucl. Acid Res., 12, 387.

The expression of the DNA polymer encoding the polypeptide in a recombinant host cell may be carried out by means of a replicable expression vector capable, in the host cell, of expressing the DNA polymer. The expression vector is novel and also forms part of the invention.

The replicable expression vector may be prepared in accordance with the invention, by cleaving a vector compatible with the host cell to provide a linear DNA segment having an intact replicon, and combining said linear segment with one or more DNA molecules which, together with said linear segment, encode the polypeptide, under ligating conditions.

The ligation of the linear segment and more than one DNA molecule may be carried out simultaneously or sequentially as desired.

Thus, the DNA polymer may be preformed or formed during the construction of the vector, as desired. The choice of vector will be determined in part by the host cell, which may be prokaryotic, such as $E.$ $coli,$ or eukaryotic, such as mouse C127, mouse myeloma chinese hamster ovary, fungi e.g. filamentous fungi or unicellular 'yeast' or an insect cell such as Drosophila. The host cell may also be in a transgenic animal. Suitable vectors include plasmids, bacteriophages, cosmids and recombinant viruses derived from, for example, baculoviruses or vaccinia.

The DNA polymer may be assembled into vectors designed for isolation of stable transformed mammalian cell lines expressing the fragment e.g. bovine papillomavirus vectors in mouse C127 cells, or amplified vectors in chinese hamster ovary cells (DNA Cloning Vol. II D. M. Glover ed. IRL Press 1985; Kaufman, R. J. et al., Molecular and Cellular Biology 5, 1750–1759, 1985; Pavlakis G. N. and Hamer, D. H. Proceedings of the National Academy of Sciences (USA) 80, 397–401, 1983; Goeddel, D. V. et al., European Patent Application No. 0093619, 1983).

The preparation of the replicable expression vector may be carried out conventionally with appropriate enzymes for restriction, polymerisation and ligation of the DNA, by procedures described in, for example, Sambrook et al., cited above. Polymerisation and ligation may be performed as described above for the preparation of the DNA polymer. Digestion with restriction enzymes may be performed in an appropriate buffer at a temperature of 20°–70° C., generally in a volume of 50 µl or less with 0.1–10 µg DNA.

The recombinant host cell is prepared, in accordance with the invention, by transforming a host cell with a replicable expression vector of the invention under transforming conditions. Suitable transforming conditions are conventional and are described in, for example, Sambrook et al., cited above, or "DNA Cloning" Vol. II, D. M. Glover ed., IRL Press Ltd, 1985.

The choice of transforming conditions is determined by the host cell. Thus, a bacterial host such as $E.$ $coli,$ may be treated with a solution of $CaCl_2$ (Cohen et al., Proc. Nat. Acad. Sci., 1973, 69, 2110) or with a solution comprising a mixture of RbCl, $MnCl_2$, potassium acetate and glycerol, and then with 3-[N-morpholino]-propane-sulphonic acid, RbCl and glycerol or by electroporation as for example described by Bio-Rad Laboratories, Richmond, Calif., USA, manufacturers of an electroporator. Mammalian cells in culture may be transformed by calcium co-precipitation of the vector DNA onto the cells or by using cationic liposomes.

The invention also extends to a host cell transformed with a replicable expression vector of the invention.

Culturing the transformed host cell under conditions permitting expression of the DNA polymer is carried out conventionally, as described in, for example, Sambrook et al., and "DNA Cloning" cited above. Thus, preferably the cell is supplied with nutrient and cultured at a temperature below 45° C.

The protein product is recovered by conventional methods according to the host cell. Thus, where the host cell is bacterial such as $E.$ $coli$ and the protein is expressed intracellularly, it may be lysed physically, chemically or enzymatically and the protein product isolated from the resulting lysate. Where the host cell is mammalian the product is usually isolated from the nutrient medium.

Where the host cell is bacterial, such as $E.$ $coli,$ the product obtained from the culture may require folding for optimum functional activity. This is most likely if the protein is expressed as inclusion bodies. There are a number of aspects of the isolation and folding process that are regarded as important. In particular, the polypeptide is preferably partially purified before folding, in order to minimise formation of aggregates with contaminating proteins and minimise misfolding of the polypeptide. Thus, the removal of contaminating *E. coli* proteins by specifically isolating the inclusion bodies and the subsequent additional purification prior to folding are important aspects of the procedure.

The folding process is carried out in such a way as to minimise aggregation of intermediate-folded states of the polypeptide. Thus, careful consideration needs to be given to, among others, the salt type and concentration, temperature, protein concentration, redox buffer concentrations and duration of folding. The exact condition for any given polypeptide generally cannot be predicted and must be determined by experiment.

There are numerous methods available for the folding of proteins from inclusion bodies and these are known to the skilled worker in this field. The methods generally involve breaking all the disulphide bonds in the inclusion body, for example with 50 mM 2-mercaptoethanol, in the presence of a high concentration of denaturant such as 8M urea or 6M guanidine hydrochloride. The next step is to remove these agents to allow folding of the proteins to occur. Formation of the disulphide bridges requires an oxidising environment and this may be provided in a number of ways, for example by air, or by incorporating a suitable redox system, for example a mixture of reduced and oxidised glutathione.

Preferably, the inclusion body is solubilised using 8M urea, in the presence of mercaptoethanol, and protein is folded, after initial removal of contaminating proteins, by addition of cold buffer. A preferred buffer is 20 mM ethanolamine containing 1 mM reduced glutathione and 0.5 mM oxidised glutathione. The folding is preferably carried out at a temperature in the range 1 to 5° C. over a period of 1 to 4 days.

If any precipitation or aggregation is observed, the aggregated protein can be removed in a number of ways, for example by centrifugation or by treatment with precipitants such as ammonium sulphate. Where either of these procedures are adopted, monomeric polypeptide is the major soluble product.

If the bacterial cell secretes the protein, folding is not usually necessary.

Peptide linkages in the derivatives of the invention may be made chemically or biosynthetically by expression of appropriate coding DNA sequences. Non peptide linkages may be made chemically or enzymatically by post-translational modification.

The polypeptide portion of the derivatives of the invention may be prepared by expression in suitable hosts of modified genes encoding the soluble polypeptide of the invention plus one or more peptide membrane binding elements and optional residues such as cysteine to introduce linking groups to facilitate post translational derivatisation with additional membrane binding elements.

The polypeptide portion of the derivative of the inversion may include a C-terminal cysteine to facilitate post translational modification. Expression in a bacterial system is preferred for proteins of moderate size (up to ~70 kDa) and with <~8 disulphide bridges. More complex proteins for which a free terminal Cys could cause refolding or stability problems may require stable expression in mammalian cell lines (especially CHO). This will also be needed if a carbohydrate membrane binding element is to be introduced post-translationally. The use of insect cells infected with recombinant baculovirus encoding the polypeptide portion is also a useful general method for preparing more complex proteins and will be preferred when it is desired to carry out certain post-translational processes (such as palmitoylation) biosynthetically (see for example, M. J. Page et al J.Biol.Chem. 264, 19147–19154, 1989).

A preferred method of handling proteins C-terminally derivatised with cysteine is as a mixed disulphide with mercaptoethanol or glutathione or as the 2-nitro, 5-carboxyphenyl thio-derivative as generally described below in Methods.

Peptide membrane binding elements may be prepared using standard solid state synthesis such as the Merrifield method and this method can be adapted to incorporate required non-peptide membrane binding elements such as N-acyl groups derived from myristic or palmitic acids at the N terminus of the peptide. In addition activation of an amino acid residue for subsequent linkage to a protein can be achieved during chemical synthesis of such membrane binding elements. Examples of such activations include formation of the mixed 2-pyridyl disulphide with a cysteine thiol or incorporation of an N-haloacetyl group. Peptides can optionally be prepared as the C-terminal amide.

The derivatives of the invention may utilise a peptide membrane binding element comprising one or more derivatisations selected from:

a terminal cysteine residue optionally activated at the thiol group;

an N-haloacetyl group (where halo signifies chlorine, bromine or iodine) located at the N-terminus of the the peptide or at an ε-amino group of a lysine residue;

an amide group at the C-terminus; and a fatty acid N-acyl group at the N-terminus or at an ε-amino group of a lysine residue.

Chemical bridging groups include those described in EP0109653 and EP0152736. The bridging group is generally of the formula:

$$-A-R-B- \qquad (V)$$

in which each of A and B, which may be the same or different, represents —CO—, —C(=NH$_2^+$)—, maleimido, —S— or a bond and R is a bond or a linking group containing one or more —(CH$_2$)— or meta- or para-disubstituted phenyl units.

Were the polypeptide portion of the derivative of the invention and a peptide membrane binding element both include a C-terminal cysteine the chemical bridging group will take the form —S—S—. The bridge is generated by conventional disulphide exchange chemistry, by activating a thiol on one polypeptide and reacting the activated thiol with a free thiol on the other polypeptide. Such activation procedures make use of disulphides which form stable thiolate anions upon cleavage of the S—S linkage and include reagents such as 2,2' dithiopyridine and 5,5'-dithio(2-nitrobenzoic acid, DTNB) which form intermediate mixed disulphides capable of further reaction with thiols to give stable disulphide linkages.

R may include moieties which interact with water to maintain the water solubility of the linkage and suitable moieties include —CO—NH—, —CO—NMe—, —S—S—, —CH(OH)—, —SO$_2$—, —CO$_2$—, —(CH$_2$CH$_2$—O)$_m$— and —CH(COOH)— where m is an integer of 2 or more.

Examples of R include —(CH$_2$)$_r$—, —(CH$_2$)$_p$—S—S—(CH$_2$)$_q$— and —(CH$_2$)$_p$—CH(OH)—CH(OH)—(CH$_2$)$_q$—, in which r is an integer of at least 2, preferably at least 4 and p and q are independently integers of at least 2.

The bridging group of formula (V) may be derived from a linking agent of formula (VI):

$$X-R_1-Y \qquad (VI)$$

in which $R_1$ is a linking group containing one or more —($CH_2$)— units and X and Y are functional groups reactable with surface amino acid groups, preferably a lysine or cysteine group, or the N-terminal amino group, or a protein attachment group.

Preferred agents are those where X and Y are different, known as heterobifunctional agents. Each end of the agent molecule is reacted in turn with each polypeptide to be linked in separate reactions. Examples of heterobifunctional agents of formula (VI) include:

N-succinimidyl 3-(2-pyridyldithio)propionate
succinimidyl 4-(N-maleimido)caproate
3-(2-pyridyl)methyl propionimidate hydrochloride In each case Y is capable of reacting with a thiol group on a polypeptide, which may be a native thiol or one introduced as a protein attachment group.

The protein attachment group is a functionality derived by modification of a polypeptide with a reagent specific for one or more amino acid side chains, and which contains a group capable of reacting with a cleavable section on the other polypeptide. An example of a protein attachment group is a thiol group. An example of a cleavable section is a disulphide bond. Alternatively the cleavable section may comprise an α, β dihydroxy function.

As an example, the introduction of a free thiol function by reaction of a polypeptide with 2-iminothiolane, N-succinimidyl 3-(2-pyridyldithio)propionate (with subsequent reduction) or N-acetyl homocysteine thiolactone will permit coupling of the protein attachment group with a thiol-reactive B structure. Alternatively, the protein attachment group can contain a thiol-reactive entity such as the 6-maleimidohexyl group or a 2-pyridyl-dithio group which can react with a free thiol in X. Preferably, the protein attachment group is derived from protein modifying agents such as 2-iminothiolane that react with lysine ε-amino groups in proteins.

When X represents a group capable of reacting directly with the amino acid side chain of a protein, it is preferably an N-succinimidyl group. When X represents a group capable of reacting with a protein attachment group, it is preferably a pyridylthio group.

In the above processes, modification of a polypeptide to introduce a protein attachment group is preferably carried out in aqueous buffered media at a pH between 3.0 and 9.0 depending on the reagent used. For a preferred reagent, 2-iminothiolane, the pH is preferably 6.5–8.5. The concentration of polypeptide is preferably high (>10 mg/ml) and the modifying reagent is used in a moderate (1.1- to 5-fold) molar excess, depending on the reactivity of the reagent. The temperature and duration of reaction are preferably in the range 0°–40° C. and 10 minutes to 7 days. The extent of modification of the polypeptide may be determined by assaying for attachment groups introduced.

Such assays may be standard protein chemical techniques such as titration with 5,5'-dithiobis-(2-nitrobenzoic acid). Preferably, 0.5–3.0 moles of protein attachment group will be introduced on average per mole of polypeptide. The modified polypeptide may be separated from excess modifying agents by standard techniques such as dialysis, ultrafiltration, gel filtration and solvent or salt precipitation. The intermediate material may be stored in frozen solution or lyophilised.

Where a protein attachment group is introduced in this way, the bridging group (V) will be formed from a reaction of the linking agent (VI) and the protein attachment group.

The polypeptides to be linked are reacted separately with the linking agent or the reagent for introducing a protein attachment group by typically adding an excess of the reagent to the polypeptide, usually in a neutral or moderately alkaline buffer, and after reaction removing low molecular weight materials by gel filtration or dialysis. The precise conditions of pH, temperature, buffer and reaction time will depend on the nature of the reagent used and the polypeptide to be modified. The polypeptide linkage reaction is preferably carried out by mixing the modified polypeptides in neutral buffer in an equimolar ratio. Other reaction conditions e.g. time and temperature, should be chosen to obtain the desired degree of linkage. If thiol exchange reactions are involved, the reaction should preferably be carried out under an atmosphere of nitrogen. Preferably, UV-active products are produced (eg from the release of pyridine 2-thione from 2-pyridyl dithio derivatives) so that coupling can be monitored.

After the linkage reaction, the polypeptide conjugate can be isolated by a number of chromatographic procedures such as gel filtration, ion-exchange chromatography, affinity chromatography or hydrophobic interaction chromatography. These procedures my be either low pressure or high performance variants.

The conjugate may be characterised by a number of techniques including low pressure or high performance gel filtration, SDS polyacrylamide gel electrophoresis or isoelectric focussing.

Membrane binding elements which are fatty acid derivatives are attached post translationally to a peptidic membrane binding element, preferably at the terminus of the polypetide chain. Preferably, where the recombinant polypeptide portion of the derivative of the invention contains the peptide membrane binding element, it has a unique cysteine for coupling to the fatty acid derivative. Where the recombinant polypeptide has a cysteine residue, a thiol-derivative of the fatty acid is added to the refolded recombinant protein at a late stage in purification (but not necessarily the final stage) and at a reagent concentration preferably below the critical micelle concentration. One of the fatty acid derivative and the recombinant peptide will have the thiol group activated as described above for thiol interchange reactions. The fatty acid derivative is preferably a fatty acyl derivative of an amino$C_{2-6}$alkane thiol (optionally C-substituted) such as N-(2-myristoyl) aminoethanethiol or N-myristoyl L-cysteine.

Suitable examples of hydrophilic synthetic polymers include polyethyleneglycol (PEG), preferably α,ω functionalised derivatives, more preferably α-amino, ω-carboxy-PEG of molecular weight between 400 and 5000 daltons which are linked to the polypeptide for example by solid-phase synthesis methods (amino group derivatisation) or by thiol-interchange chemistry.

Membrane binding elements derived from ligands of known integral membrane proteins, either amino acid sequences or carbohydrates, may be generated by post-translational modification using the glycosylation pathways of eukaryotic cells targeted to N-linked glycosylation sites in the peptide sequence.

Convenient generic final stage purification strategies are hydrophobic interaction chromatography (HIC) on C2–C8 media and cation exchange chromatography for separation of derivatised and underivatised proteins into which a hydrophobic electrostatic switch combination has been inserted.

In a further aspect, therefore, the invention provides a process for preparing a derivative according to the invention which process comprises expressing DNA encoding the polypeptide portion of said derivative in a recombinant host cell and recovering the product and thereafter post translationally modifying the polypeptide to chemically introduce membrane binding elements.

The invention also extends to DNA encoding the polypeptide portion of the derivative and to replicable expression vectors and recombinant host cells containing the DNA.

The polypeptide or derivative of this invention is useful in the treatment or diagnosis of many complement-mediated or complement-related diseases and disorders including, but not limited to, those listed below.

Disease and Disorders Involving Complement
Neurological Disorders
multiple sclerosis
stroke
Guillain Barre Syndrome
traumatic brain injury
Parkinson's disease
allergic encephalitis
Alzheimer's disease Disorders of Inappropriate or Undesirable Complement Activation
haemodialysis complications
hyperacute allograft rejection
xenograft rejection
corneal graft rejection
interleukin-2 induced toxicity during IL-2 therapy
paroxysmal nocturnal haemoglobinuria Inflammatory Disorders
inflammation of autoimmune diseases
Crohn's Disease
adult respiratory distress syndrome
thermal injury including burns or frostbite
uveitis
psoriasis
asthma
acute pancreatitis
Kawasaki's disease Post-Ischemic Reperfusion Conditions
myocardial infarction
balloon angioplasty
atherosclerosis (cholesterol-induced) & restenosis
hypertension
post-pump syndrome in cardiopulmonary bypass or renal haemodialysis
renal ischemia
intestinal ischaemia Infectious Diseases or Sepsis
multiple organ failure
septic shock Immune Complex Disorders and Autoimmune Diseases
rheumatoid arthritis
systemic lupus erythematosus (SLE)
SLE nephritis
proliferative nephritis
glomerulonephritis
haemolytic anemia
myasthenia gravis Reproductive Disorders
antibody- or complement-mediated infertility Wound Healing The present invention is also directed to a pharmaceutical composition comprising a therapeutically effective amount of a polypeptide or derivative, as above, and a pharmaceutically acceptable carrier or excipient.

The present invention also provides a method of treating a disease or disorder associated with inflammation or inappropriate complement activation comprising administering to a subject in need of such treatment a therapeutically effective amount of a polypeptide or derivative of this invention.

In the above methods, the subject is preferably a human.

An effective amount of the polypeptide or derivative for the treatment of a disease or disorder is in the dose range of 0.01–100 mg/kg; preferably 0.1 mg–10 mg/kg.

For administration, the polypeptide or derivative should be formulated into an appropriate pharmaceutical or therapeutic composition. Such a composition typically contains a therapeutically active amount of the polypeptide or derivative and a pharmaceutically acceptable excipient or carrier such as saline, buffered saline, dextrose, or water. Compositions may also comprise specific stabilising agents such as sugars, including mannose and mannitol, and local anaesthetics for injectable compositions, including, for example, lidocaine.

Further provided is the use of a polypeptide or derivative of this invention in the manufacture of a medicament for the treatment of a disease or disorder associated with inflammation or inappropriate complement activation.

In order to inhibit complement activation and, at the same time, provide thrombolytic therapy, the present invention provides compositions which further comprise a therapeutically active amount of a thrombolytic agent. An effective amount of a thrombolytic agent is in the dose range of 0.01–10 mg/kg; preferably 0.1–5 mg/kg. Preferred thrombolytic agents include, but are not limited to, streptokinase, human tissue type plasminogen activator and urokinase molecules and derivatives, fragments or conjugates thereof. The thrombolytic agents may comprise one or more chains that may be fused or reversibly linked to other agents to form hybrid molecules (EP-A-0297882 and EP 155387), such as, for example, urokinase linked to plasmin EP-A-0152736), a fibrinolytic enzyme linked to a water-soluble polymer (EP-A-0183503). The thrombolytic agents may also comprise muteins of plasminogen activators (EP-A-0207589). In a preferred embodiment, the thrombolytic agent may comprise a reversibly blocked in vitro fibrinolytic enzyme as described in U.S. Pat. No. 4,285,932. A most preferred enzyme is a p-anisoyl plasminogen-streptokinase activator complex as described in U.S. Pat. No. 4,808,405, and marketed under the Trademark EMINASE (generic name anistreplase, also referred to as APSAC; Monk et al., 1987, Drugs 34:25–49).

Routes of administration for the individual or combined therapeutic compositions of the present invention include standard routes, such as, for example, intravenous infusion or bolus injection. Active complement inhibitors and thrombolytic agents may be administered together or sequentially, in any order.

The present invention also provides a method for treating a thrombotic condition, in particular acute myocardial infarction, in a human or non-human animal. This method comprises administering to a human or animal in need of this treatment an effective amount of a polypeptide or derivative according to this invention and an effective amount of a thrombolytic agent.

Also provided is the use of a polypeptide or derivative of this invention and a thrombolytic agent in the manufacture of a medicament for the treatment of a thrombotic condition in a human or animal. Such methods and uses may be carried out as described in WO 91/05047.

This invention further provides a method for treating adult respiratory distress syndrome (ARDS) in a human or non-human animal. This method comprises administering to the patient an effective amount of a polypeptide or derivative according to this invention.

The invention also provides a method of delaying hyperacute allograft or hyperacute xenograft rejection in a human or non-human animal which receives a transplant by administering an effective amount of a polypeptide or derivative according to this invention. Such administration may be to the patient or by application to the transplant prior to implantation.

The invention yet further provides a method of treating wounds in a human or non-human animal by administering by either topical or parenteral e.g. intravenous routes, an effective amount of a polypeptide or derivative according to this invention.

GENERAL METHODS USED IN EXAMPLES (i) DNA Cleavage

Cleavage of DNA by restriction endonucleases was carried out according to the manufacturer's instructions using supplied buffers. Double digests were carried out simultaneously if the buffer conditions were suitable for both enzymes. Otherwise double digests were carried out sequentially where the enzyme requiring the lowest salt condition was added first to the digest. Once the digest was complete the salt concentration was altered and the second enzyme added.

(ii) DNA Ligation

Ligations were carried out using T4 DNA ligase purchased from Promega, as described in Sambrook et al, (1989) Molecular Cloning: A Laboratory Manual 2nd Edition. Cold Spring Harbour Laboratory Press.

(iii) Plasmid Isolation

Plasmid isolation was using Promega Wizard™ Plus Minipreps or Qiagen Plasmid Maxi kit according to the manufacture's instructions.

(iv) DNA Fragment Isolation

DNA fragments were excised from agarose gels and DNA extracted using the QIAEX gel extraction kit or Qiaquick, or GeneClean gel extraction kits according to the manufacturer's instructions (QIAGEN Inc., USA, Bio 101 Inc, USA).

(v) Introduction of DNA into *E. coli*

Plasmids were transformed into *E. coli* BL21(DE3) (Studier and Moffat, (1986), *J. Mol. Biol* 189:113) that had been made competent using calcium chloride as described in Sambrook et al, (1989). *E. coli* JM109 and XL 1-blue strains were purchased as a frozen competent culture from Promega.

(vi) DNA Sequencing

Plasmid DNA is sequenced on a Vistra DNA Labstation 625. The sequencing chemistry is performed using Amersham International's 'Thermo Sequenase fluorescent dye-terminator cycle sequencing kit' (RPN 2435), in conjunction with their 'FMP fluorescent dye-terminator precipitation kit' (RPN 2433) according to the manufacturer's instructions.

The sequences produced by the above procedure are analysed by a Perkin Elmer ABI Prism 377 DNA Sequencer. This is an eletrophoretic technique using 36 cm×0.2 mm 4% acrylamide gels, the fluorescently labeled DNA fragments being detected by a charge coupled device camera according to the manufacturer's instructions.

(vii) Production of Oligonucleotides

Oligonucleotides were purchased from Cruachem.

(viii) pBROC413

The plasmid pT7-7 [Tabor, S (1990), Current Protocols in Molecular Biology, F. A. Ausubel, Brent, R. E. Kingston, D. D. Moore, J. G. Seidman, J. A. Smith, and K. Struhl.eds.] pp.16.2.1–16.2.11, Greene Publishing and Wiley-interscience,New York.] contains DNA corresponding to nucleotides 2065–4362 of pBR322 and like pBR322 can be mobilized by a conjugative plasmid in the presence of a third plasmid ColK. A mobility protein encoded by ColK acts on the nic site at nucleotide 2254 of pBR322 initiating mobilization from this point. pT7-7 was digested with LspI and BglII and the protruding 5' ends filled in with the Klenow fragment of DNA PolymeraseI. The plasmid DNA fragment was purified by agarose gel electrophoresis, the blunt ends ligated together and transformed into *E. coli* DH1 by electroporation using a Bio-Rad Gene Pulser and following the manufacturers recommended conditions. The resultant plasmid pBROC413 was identified by restriction enzyme analysis of plasmid DNA.

The deletion in pBROC413 from the LspI site immediately upstream of the f 10 promoter to the BglII site at nucleotide 434 of pT7-7 deletes the DNA corresponding to nucleotides 2065–2297 of pBR322. The nic site and adjacent sequences are therefore deleted making pBROC413 non mobilizable.

(ix) Sodium Dodecyl Sulphate Polyacrylamide Gel Electrophoresis (SDS PAGE)

SDS PAGE was carried out generally using the Novex system (British Biotechnology) according to the manufacturer's instructions. Prepacked gels of acrylamide concentrations 4–20% were most frequently used. Samples for electrophoresis, including protein molecular weight standards (for example LMW Kit, Pharmacia or Novex Mark 12) were usually diluted in 1% (w/v)SDS-containing buffer (with or without 5% (v/v) 2-mercaptoethanol), and left at room temperature for about 0.5 h before application to the gel.

(x) Reduction of Disulphides and Modification of Thiols in Proteins

There are a number of methods used for achieving the title goals. The reasons it may be necessary to carry out selective reduction of disulphides is that during refolding, concentration and further purification of multi-thiol proteins inappropriate disulphide pairing can occur. In addition, even if correct disulphide paring does occur, it is possible that a free cysteine in the protein may become blocked with the reducing agent, for example glutathione. These derivatives are generally quite stable. In order to make them more reactive, for example for subsequent conjugation to another functional group, they need to be selectively reduced, with for example dithiothreitol (DTT) or with Tris(2-carboxyethyl) phosphine.HCl (TCEP) then optionally modified with a function which is moderately unstable. An example of the latter is Ellmans reagent (DTNB) which gives a mixed disulphide, in the case where treatment with DTNB is omitted, careful attention to experimental design is necessary to ensure that dimerisation of the free thiol-containing protein is minimised. Reference to the term 'selectively reduced' above means that reaction conditions eg. duration, temperature, molar ratios of reactants have to be carefully controlled so that disulphide bridges within the natural architecture of the protein are not reduced. All the reagents are commercially available eg. from Sigma or Pierce.

The following general examples illustrate the type of conditions that may be used and that are useful for the generation of free thiols and their optional modification. The specific reaction conditions to achieve optimal thiol reduction and/or modification are ideally determined for each protein batch.

TCEP may be prepared as a 20 mM solution in 50 mM Hepes (approx. pH 4.5) and may be stored at −40 degrees C. DTT may be prepared at 10 mM in sodium phosphate pH 7.0 and may be stored at −40 degrees C. DTNB may be prepared at 10 mM in sodium phosphate pH 7.0 and may be stored at −40 degrees C. All of the above reagents are typically used at molar equivalence or molar excess, the precise concentrations ideally identified experimentally. The duration and the temperature of the reaction are similarly determined experimentally. Generally the duration would be in the range 1 to 24 hours and the temperature would be in the range 2 to 30 degrees C. Excess reagent may be conveniently removed by buffer exchange, for example using Sephadex G25. A suitable buffer is 0.1M sodium phosphate pH 7.0.

EXAMPLES

Example 1

Expression and isolation of CM7 (SEQ NO: ID 1)
(a) Construction of plasmid pBrocSCR1-3CM7 encoding CM7

CM7 consists of the short consensus repeats 1 and 2 from the CR1 gene fused to the sequence of SCR3 from the CR1-like gene. The sequence of the DNA encoding CM7 is shown in SEQ ID NO: 2. It was constructed using the plasmid coding for SCR1-3 (MQ1→K196) of CR-1, pDB1013-5 (Ref: patent application WO 94/00571). PDB1013-5 was subjected to site directed mutagenesis using a QuickChange kit suppled by Stratagene. Three pairs of oligonucleotides were utilised to introduce ten amino acid changes changes to the native SCR3 sequence corresponding to the changes observed in the CR-1 like pseudogene sequence described by Hourcade et al 1990 (Journal of Biological Chemistry 265, pp 974–980): Each pair of oligonucleotides is complementary in sequence. Changes are shown in lower case.

The first pair:

CGACCAT CgCCAACGGTGATTTC AcCTCTAtCAgTCGC-
GAGtATTTTCAC   (SEQ ID NO: 3)

and

GTGAAAATaCTCGCGAcTGaTAGAGgT-
GAAATCACCGTTGGcGATGGTCG   (SEQ ID NO: 4)

resulted in five amino acid changes and loss of an ApoI restriction site.

The second pair:

GACCTACCaCTGCAATCtGGGTAGC-
cGTGGTaaaAAGGTGTTTGAGC   (SEQ ID NO: 5)

and

GCTCAAACACCTTtttACCACgGCTAC-
CCaGATTGCAGtGGTAGGTC   (SEQ ID NO: 6)

resulted in four amino acid changes and the acquisition of a BsaII vrestriction site.

The third pair:

GCACTAGcAAaGACGATCAAGTGGG   (SEQ ID NO: 7)

and

CCCACTTGATCGTCt TTgCTAGTGC   (SEQ ID NO: 8)

resulted in a single amino acid change and the loss of a SpeI restriction site.

To generate DNA encoding CM7 all six oligonucleotides were used simultaneously in the mutagenesis reaction and transformed into competent XL 1-Blue E. coli (Stratagene). Resulting colonies were grown up in LBroth and plasmids extracted using standard methodology. The plasmids were screened for successful mutagenesis by the loss of the ApoI or SpeI restriction sites or the acquisition of a new BsaII vrestriction site. In the first experiment only the oligonucleotide pair (SEQ ID NOS: 7 and 8) were incorporated resulting in the loss of the SpeI restriction site. This plasmid (pBrocSCR1-3P3) was subjected to further rounds of site-directed mutagenesis using the oligonucleotides SEQ ID NOS 3, 4, 5 and 6. From this was produced the mutated plasmid pBrocSC1-3P7 containing all ten amino acid coding changes in the SCR3 coding domain.

Using the restriction enzymes EcoRI and HindIII, the mutated SCR3 domain was excised from the plasmid pBrocSCR1-3P7 as a 229 base pair fragment and ligated back into a 2540 base pair EcoRI/HindIII fragment of pDB1031-5 containing vector and SCR1–2 sequences to minimise the possibility of unwanted mutations elsewhere in the plasmid. The resulting plasmid was pBrocSCR1-3CM7 encoding the protein CM7 (SEQ ID NO: 1).

(b) Expression of CM7 from pBrocSCR1-3CM7 pBrocSCR1-3CM7 was transformed into calcium chloride competent E. coli BL21(DE3) and resultant colonies were isolated and checked for plasmid content. To express protein from pBrocSCR1-3CM7 in E. coli BL21(DE3), a single colony was inoculated into 10 ml LB-phosphate media (20 g/L tryptone, 15 g/L yeast extract. 0.8 g/L NaCl, 0.2 g/L $Na_2HPO_4$, 0.1 g/L $KH_2PO_4$) containing 50 ug/ml ampicillin. The culture was grown for 6 hours at 37° C., 230 r.p.m. before being used to inoculate 100 ml of the same media containing 50 ug/ml ampicillin. Growth was under the same conditions overnight. 25 ml of each culture were then used to inoculate 600 ml of the same media with 50 ug/ml ampicillin in 3 L Erlenmeyer flasks. Cells were grown to an OD of about 0.25 at $A_{600}$ nm. IPTG (isopropyl B-D galactopyranoside) was added to a final concentration of 1 mM and cells allowed to continue growth for a further about 8 hours before harvesting by centrifugation at 8000 g/10 min. Pellet from 2L of culture was stored at −40° C.

(c) Isolation, Refolding, Purification and Formulation of CM7

The methods described are essentially those detailed in Dodd I. et al (1995) Protein Expression and Purification 6 727–736 with some modifications.

(i) Isolation of Solubilised Inclusion Bodies

The frozen cell pellet of E. coli BL21(DE3) (pBrocSCR1-3CM7) was allowed to thaw at room temperature for 2 h and resuspended in 50 mM Tris/50 mM NaCl/1 mM EDTA pH 8.0 (approx. 60 ml). The suspension was transferred to a glass beaker surrounded by ice and sonicated (Heat systems—Ultrasonics W380; 50×50% pulse, pulse time=5 sec.) for 3 min. and then spun at 7000 rpm for 20 min. The supernatant was decanted and discarded The pellet was resuspended in 20 mM Tris/8M urea/1 mM EDTA/50 mM 2-mercaptoethanol pH 8.5 (80 ml) at room temperature by vigorous swirling, then left for 1 h at room temperature with occasional swirling.

(ii) Initial Purification Using SP-Sepharose

To the viscous solution was added SP-Sepharose FF (30 g wet weight) that had been water washed and suction-dried. The mixture was swirled vigorously and left static for 1–2 h at room temperature. The supernatant was decanted, sampled and discarded. The remaining slurry was resuspended to a uniform suspension and poured into a glass jacket and allowed to settle into a packed bed. The column was equilibrated with 0.02M Tris/8M urea/0.05M 2-mercaptoethanol/0.001 M EDTA pH 8.5.at room temperature. When the $A_{280}$ of the eluate had stabilised at baseline, the buffer was changed to equilibration buffer additionally containing 1M NaCl. A single $A_{280}$ peak was eluted by the 1M NaCl-containing buffer; the volume was approx. 40 ml. The protein concentration of a sample of this solution that had been buffer-exchanged (Sephadex G25) into 50 mM formic acid was estimated by $A_{280}$ determination, using a molar extinction coefficient of 25000 $cm^{-1}$ and the formula A=ECL where A is the absorption of the solution at 280 nm, E is the molar extinction coefficient C is the molar concentration of protein and L is the light path in cm. This showed the product had a protein concentration of 0.44 mg/ml. SDS PAGE showed that the product contained apparently two major species, both with a molecular weight around 22 000. The solution was stored at −40° C.

(iii) Folding and Further Processing

The 40 ml SP-Sepharose-purified product was added gradually over a 1 min period to 1240 ml freshly prepared, cold 0.06 M ethanolamine/1 mM EDTA with continuous swirling, and left static for 1 h/4° C. Reduced glutathione (GSH) was added to 1 mM and oxidised glutathione (GSSG) was added to 0.5 mM by the addition of 100-fold concentrates of both solutions. The solution was clear and was left static approx 2–3° C. for 5 d. The solution was then ultrafiltered using a YM10 membrane to a final retentate volume of 59 ml; the retentate was clear and it was mixed with 9 vol. 0.1M $NaH_2PO_4$/1M $(NH_4)_2SO_4$ pH 7.0 (Buffer A) at room temperature and immediately centrifuged at 3000 rpm for 20 min. The supernatant was applied to a column (i.d.,26 mm, h.,100 mm) of Butyl Toyopearl 650M and the column was developed using a linear gradient of Buffer A to0.1M sodium phosphate pH 7.0. All the chromatography was at room temperature at 2 ml/min. A single A280-peak was noted during the gradient. The fractions spanning the peak were pooled and were ultrafiltered (YM10) to 2.5 ml. This retentate was regarded as the product. The product contained one major species by non-reduced SDS PAGE with an estimated purity of >95% and an apparent molecular weight of 21 000. A sample of the product diluted 10-fold in 0.1M sodium phosphate pH7.0 had an A280 of 0.47; using an extinction coefficient of 34000 allowed the protein concentration to be calculated as 140 uM. C18 Poros HPLC using a acetonitrile gradient in 0.08% TFA gave a single A215 peak with an estimated purity of approx. 99%. Electrospray mass spectrophotometry gave a mass of 21887.

Example 2

Construction of Plamids pBrocSCR1-3CM1, 2, 3, 5 and 6 Encoding CM1, CM2, CM3, CM5 and CM6

These constructs contain some but not all of the CR1-like gene changes in the SCR3 region of SCR1-3 of CR1. The plasmids pBrocSCR1-3P1, 2, 3, 5 and 6 were generated by site directed mutagenesis using the method described in Example 1a) using different combinations of oligonucleotide pairs:

pBrocSCR1-3P1 was made using only SEQ ID NOS 3 and 4 pBrocSCR1-3P2 was made using only SEQ ID NOS 5 and 6 pBrocSCR1-3P3 was made using only SEQ ID NOS 7 and 8 pBrocSCR1-3P5 was made using SEQ ID NOS 5 to 8 and pBrocSCR1-3P6 was made using SEQ ID NOS 3, 4, 7 and 8

Plasmids pBrocSCR1-3CM1, 2, 3, 5 and 6 were generated by excision of 229 base pair fragments encoding the mutated SCR3 domains from plasmids pBrocSCR1-3P1 to pBrocSCR1-3P6 and the fragments were ligated back into a 2540 base pair EcoRI/HindIII fragment of pDB1013-5 containing vector and SCR1–2 sequences to minimise the possibility of unwanted mutations elsewhere in the plasmid. The resulting plasmids were pBrocSCR1-3CM1, 2, 3, 5 and 6, encoding the proteins CM1, CM2, CM3, CM5 and CM6 (SEQ ID NOS 9, 11, 13, 15 and 17, respectively). The DNA sequences encoding these polypeptides is shown in SEQ ID NOS. 10, 12, 14, 16 and 18.

CM1, CM2, CM3, CM5 and CM6 were expressed in *E. coli* using methods similar to those described for CM7 in Example 1. Analysis of total cell lysate by SDS PAGE followed by staining for protein showed that the IPTG treatment led to marked expression of a polypeptide with a molecular weight of about 22 000, which was indistinguishable from CM7 analysed in the same way. The whole cell pellet may be stored at −40 degrees C. or below until required.

The *E. coli* cell pellet can be processed in exactly the same way as described for CM7 to obtain purified, concentrated protein for further evaluation.

Example 3

(i)Construction of Plasmids pBrocSCR3CM8, 9, 10, 12, 13 and 14 encoding CM8, CM9, CM10, CM12, CM13 and CM14 (SEQ ID NOS: 19, 21, 23, 25, 27 and 29)

These constructs comprise a single SCR corresponding to SCR3 of CR1 and containing varying numbers of changes to CR1-like sequences. CM14 is therefore SCR3 from the CR1-like gene. The plasmids pBrocSCR3CM8, 9, 10, 12, 13 and 14 were generated from the plasmids pBrocSCR1-3P1, 2, 3, 5, 6 and 7 and the plasmid pBroc435 (Ref: patent application WO 94/00571). Digestion of pBrocSCR1-3P1, 2, 3, 5, 6 and 7 with the restriction enzymes EcoRI and HindIII yielded fragments of 229 base pairs encoding the mutated SCR3 domains from pBrocSCR1-3P1, 2, 3, 5, 6 and 7, and these were ligated with a EcoRI/HindIII fragment of 2171 base pairs from pBroc435 containing vector and promoter sequences. The resulting plasmids were pBrocSCR3CM8, 9, 10, 12, 13 and 14, encoding the proteins CM8, CM9, CM10, CM12, CM13 and CM14 (SEQ ID NOS: 19, 21, 23, 25, 27 and 29, respectively), i.e., mutant SCR3 domains identical in sequence to the SCR3 domains of CM1, CM2, CM3, CM5, CM6 and CM7. The DNA sequences encoding CM8, CM9, CM10, CM12, CM13 and CM14 are given in SEQ ID NOS. 20, 22, 24, 26, 28 and 30.

CM8, CM9, CM10, CM12 and CM13 may be expressed in *E. coli* using methods similar to those described for CM7 in Example 1. The whole cell pellet may be stored at −40 degrees C. or below until required.

The *E. coli* cell pellet can be processed in a similar way to that described for CM7 cell pellet to obtain purified, concentrated protein for further evaluation. More preferably, modifications may be made to the isolation protocol, for example those described in Clark, N. S, 1996 (Ph. D. Thesis, Southampton University).

(ii) Expression and Isolation of Protein CM14 (SEQ ID NO:29)

Using methods similar to those described for CM7 in Example 1 plasmid pBrocSCR3CM14 was used to transform competent *E.coli* BL21(DE3) strain and CM14 protein was expressed The whole cell pellet was stored at −40 degrees C. until use.

CM14 protein was isolated from the *E. coli* cell pellet initially in a similar way to that described for CM7. In brief, the inclusion bodies were isolated and they were solubilised in fully reducing buffer. 40 g ammonium sulphate was added to 200 ml of the solubilsed inclusion bodies; after stirring for 2 h at RT the 0–20% precipitate was isolated by centrifugation. This precipitate was solubilised in 8M urea/50 mM 2-mercaptoethanol-containing buffer, the preparation contained a major protein band by SDS PAGE under non-reducing conditions with an apparent molecular weight of about 7000.

Example 4

Expression and Isolation of CM7/cys (SEQ ID NO:31)

Construction of plasmid pBrocSCR1-3CM7,mutcys encoding CM7/cys. The plasmid pBrocSCR1-3CM7 mutcys was produced by site directed mutagenesis of pBrocSCR1-3CM7 using methods similar to those described in example 1. A pair of oligonucleotides with complementary sequence were used in which five changes to the sequence of pBrocSCR1-3CM7 had be introduced. Two of the changes introduced a unique ApaI restriction enzyme site without altering the amino sequence and three changes introduced a cysteine codon immediately prior to the stop codon. The sequences of the oligonuclotides used for the mutagenesis were as follows: SEQ ID NO: 32
CTGGAGCGGgCCcGCACCGCAGTGCATCATCCCGA ACAAAtgcTAATAAAAGC, SEQ ID NO: 33
GCTTTTATTAgcaTTTGTTCGGGATGATGCACTG CGGTGCgGGcCCGCTCCAG.
Following site directed mutagenesis and transformation into competent *E. coli,* the resulting colonies were analysed by restriction enzyme digestion for the introduction of the new ApaI restriction site. DNA sequencing confirmed that the encoded amino acid sequence had been altered by the addition of a single C-terminal cysteine residue to give SEQ ID NO: 31.

(ii) Expression and Isolation of CM7/cys Protein

CM7/cys was expressed in *E. coli* transformed with pBrocSCR1-3CM7 mutcys using methods identical to those described for CM7 in Example 1. The cell pellet from 1L was stored at −40 degrees C. until use.

The *E. coli* cell pellet was processed in exactly the same way as described for CM7 to obtain purified, concentrated protein for further evaluation. The final formulated protein product—the ultrafiltered retentate of the Butyl Toyopearl-eluted fractions—contained 12 mg protein based on A280 determination using an extinction coefficient of 34000 and had an apparent molecular weight and purity on SDS PAGE gels (non-reduced) of 20000 and about 80% respectively.

Example 5

Preparation of [CM7]-Cys-S-S-[MSWP-1] (PM-9) (SEQ ID NO: 34)

(i) Myristoyl/Electrostatic Switch Peptide Reagent 1 (MSWP-1)

N-(Myristoyl)-Gly-Ser-Ser-Lys-Ser-Pro-Ser-Lys-Lys-Lys-Lys-Lys-Lys-Pro-Gly-Asp-(S-2-Thiopyridyl)Cys-NH$_2$ The peptide Gly-Ser-Ser-Lys-Ser-Pro-Ser-Lys-Lys-Lys-Lys-Lys-Pro-Gly-Asp-Cys-NH$_2$ (SEQ ID NO:35)

was prepared using solid phase synthesis via the general Fmoc/tBu strategy developed by Sheppard and Atherton (E. Atherton and R. C. Sheppard, Solid Phase Synthesis, I RL Press, Oxford, 1989). Kieselguhr-supported polydimethylacrylamide resin (Macrosorb 100) was used as the solid support and was derivatised with ethylene diamine.

Coupling reactions were carried out using N-α-Fmoc protected reagents pre-activated with N,N'-diisopropylcarbodiimide N-hydroxybenzotriazole (in 4-fold molar excess) with bromophenol blue monitoring. Fmoc cleavages used 20% piperidine in DMF. Reactions to assemble the peptide chain were carried out by repeated cycles of coupling and deprotection including the attachment of the modified Rink linkage reagent (p-[(RS)-α-[1-(9H-fluoreny-9-yl-methoxyformamido]2,4 dimethoxybenzyl]-phenoxyacetic acid) designed to yield a C-terminal amide on final cleavage. The side chain functionalities of the individual amino-acids were protected as follows:

Ser (tButyl), Lys (Boc), Asp (O-tButyl), Cys (Trityl).

On completion of the peptide assembly and with the peptide still attached to the resin, the myristoyl group was arached to the amino group of the N terminal glycine by direct coupling of myristic acid by the same activation procedure. This modified peptide was then cleaved from the resin and the side-chain protecting groups removed at the same time by treatment with trifluoroacetic acid containing 2.5% water and 2.5% triisopropyl silane.

The crude product was treated with 2,2' dithiopyridine in 0.01M ammonium acetate solution at pH 8–9 for approx. 2 h, then acidified with acetic acid and purified by preparative high performance liquid chromatography (HPLC) in 0.1% trifluoracetic acid (TFA)/water and 0.1% TFA/acetonitrile as gradient component. After lyophilisation, the peptide was a white amorphous powder, soluble to at least 10 mm/ml in dimethylsulphoxide. Fast atom bombardment mass spectrometry gave main peeks at m/e 2107.8, 2129.7 and 2145.8, corresponding to the monoprotonated, monosodiated and monopotassiated molecular ions of the peptide. The 2-thiopyridyl content of the peptide was measured by dissolving it to around 0.03 mM to 0.2 mM in 0.1M Sodium Borate pH 8.0 and reducing by addition of dithiothreitol to 5 mM. The change in optical density at 343 nm was used to calculate the amount of pyridine 2-thione released using an extinction coefficient at this wavelength of 8080 cm$^{-1}$ M$^{-1}$. This indicated that the peptide content was approximately 60% of the dry weight.

H$_2$N-[CM7]-Cys-OH
|
S
|
S
|
N-(myristoyl)-Gly-Ser-Ser-Lys-Ser-Pro-Ser-Lys-Lys-Lys-Lys-Lys-Pro-Gly-Asp-Cys-NH$_2$ (ii) Synthesis of PM9

CM7/cys from Example 4 (12 uM; 0.1 ml) was mixed with TCEP (Tris-(2-carboxyethyl)phosphine) (5 mM; 0.001 ml) and incubated at room temperature for 18 h. 0.01 ml of 500 mM ethanolamine was added and mixed. MSWP-1 from (i) (2 mM in 0.1M sodium phosphate pH 7.0; 0.0014 ml) was added and the solution incubated for a further 4 h. The product was analysed by SDS PAGE and showed two primary bands under non-reducing conditions, the major one with an apparent molecular weight of 20000 and a minor one of about 22000, the latter consistent with the formation of target PM9.

Example 6

Expression and Isolation of Protein CM15/cys
(SEQ ID NO:36)

CM15-cys (SEQ ID NO:36) comprises SCR1-3 with all amino acid changes corresponding to the CR-1 like pseudogene sequence described by Hourcade et al 1990 (Journal of Biological Chemistry 265, pp 974–980) where they appear in the region homologous to SCR1-3 (13 amino acid changes in addition to the 10 changes in CM7)with an additional C-terminal cysteine residue. Plasmid pBrocSCR1-3CM15-cys was generated by site-directed mutagenesis of pBrocSCR1-3CM7/cys (Example 4). Oligonucleotides 20 to 74 bases in length and spanning the regions of change on both strands were synthesised, in which minimal base were introduced to alter the amino acid sequence and generate or delete restriction sites for diagnostic purposes. pBrocSCR1-3CM15-cys was constructed using these oligonucleotides and methodology similar to that used to construct pBrocSCR1-3CM7, as described in Example 1a). Six pairs of oligonucleotides were utilised to introduce thirteen amino acid changes changes to the native SCR1 and SCR2 sequence corresponding to the changes observed in the CR-1 like pseudogene sequence described by Hourcade et al 1990 (Journal of Biological Chemistry 265, pp 974–980): Each pair of oligonucleotides is complementary in sequence. Changes are shown in lower case.

The first pair:

CAGTGCAACGtGCCGGAATGG    (SEQ ID NO: 37)

and

CCATTCCGGAaCGTTGCACTG    (SEQ ID NO: 38)

resulted in one amino acid changes and the insertion of a Psp1406I restriction site.

The second pair: GACTGATGAtTTTGAGTTCC (SEQ ID NO: 39) and

GGAACTCAAAaTCATCAGTC    (SEQ ID NO: 40)

resulted in one amino acid change and the loss of an ApoI restriction site.

The third pair:

GTCTGGACTaGTGCTAAGGACaagTG-
        CaaACGTAAATCTTGTCG    (SEQ ID NO: 41)

and

CGACAAGATTTACGTttGCActtGTCCT-
        TAGCACtAGTCCAGAC    (SEQ ID NO: 42)

resulted in three amino acid changes and the insertion of a SpeI restriction site.

The fourth pair:

CGGCATGGcGCATGTGATCAAAGatATC-
        CAGTTCcGaTCgCAAATTAAATATTCT-
        TGTcCTAAgGGTTACCGTC    (SEQ ID NO: 43)

and

GACGGTAACCcTTAGgACAAGAATATT-
        TAATTTGcGAtCgGAACTG-
        GATatCTTTGATCACATGCgCCATGCCG    (SEQ ID NO: 44)

resulted in four amino acid changes and the insertion of EcoRV, PvuI and Bsu36I restriction sites.

The fifth pair:

CATCTCTGGTaATACTGTCATTTGG-
        GATAATaAAACACCGgTTTGTGACC    (SEQ ID NO: 45)

and

GGTCACAAAcCGGTGTTTtATTATC-
        CCAAATGACAGTATtACCAGAGATG    (SEQ ID NO: 46)

resulted in three amino acid changes and the insertion of an AgeI restriction site The sixth pair:

GACCGAATTatcTGTGGTCTG    (SEQ ID NO: 47)

and

CAGACCACAgatAATTCGGTC    (SEQ ID NO: 48)

resulted in one amino acid change and the loss of EcoRI and ApoI restriction sites.

To generate DNA encoding CM15/cys all twelve oligonucleotides were used simultaneously in the mutagenesis reaction and transformed into competent XL1-Blue E. coli (Stratagene). Resulting colonies were crown up in LBroth and plasmids extracted using standard methodology. The plasmids were screened for sucessful mutagenesis the restriction site changes. In the first experiment four of the oligonucleotide pairs were incorporated (SEQ ID NOS 37/38, 39/40, 41/42, 43/44) were incorporated. This plasmid (pBrocSCR1-3CM21-cys) was subjected to further rounds of site-directed mutagenesis using the oligonucleotides SEQ ID NOS 45/46 and 47/48. From this was produced the mutated plasmid pBrocSC1-3CM15-cys containing all thirteen amino acid coding changes in the SCR1 and SCR2 coding domain. The sequence was confirmed by DNA sequencing. In addition a plasmid encoding SCR1-3/cys with all the pseudogene changes with the exception of the Isoleucine124 Proline substitution at the hinge region separating SCR2 and SCR3 as constructed from pBrocSCR1-3CM21-cys by site directed mutagenesis with oligonucleotides SEQ ID NOS 45 and 46.

CM15/cys protein was expressed from pBrocSCR1-3CM15/cys in E. coli using methods similar to those described for CM7 in Example 1. The whole cell pellet was stored at −40 degrees C. until use.

CM15/cys protein was isolated from the E. coli cell pellet in exactly the same way as described for CM7 to obtain purified, concentrated CM15/cys protein for further evaluation. The final preparation contained a major protein band by SDS PAGE under non-reducing conditions with an apparent molecular weight of about 20000.

Example 7

Preparation of [CM15]-Cys-S-S-[MSWP-1] (SEQ ID NO:49)

The title compound is prepared from CM15/cys by procedures described in Example 5.

Example 8

Expression and Isolation of Protein CM16/cys (SEQ ID NO:50)

CM16/cys is CM15/cys with the modification I124P(i.e wild-type sequence at the hinge region between SCR2 and SCR3) The plasmid pBrocSCR1-3CM16cys was generated as described in example 6.

CM16/cys protein was expressed from pBrocSCR1-3CM16/cys in *E. coli* using methods similar to those described for CM7 in Example 1. The whole cell pellet was stored at −40 degrees C. until use.

CM16/cys protein was isolated from the *E. coli* cell pellet in a similar way to that described for CM15/cys, although or one occasion the protein was precipitated by the ammonium sulphate treatment. The final preparation contained a major protein band by SDS PAGE under non-reducing conditions with an apparent molecular weight of about 20000.

Example 9

Preparation of [CM16]-Cys-S-S-[MSWP-1] (SEQ ID NO:51)

The title compound is prepared from CM16/cys by procedures described in Example 5.

Example 10

Construction of Plasmid pBrocSCR1-3CM7rgdcys Encoding CM7/rgdcys

This construct consists of the sequence of CM7 modified at the C-terminus of the protein to contain an RGD sequence as a ligand for Glyoprotein IIb/IIIa of platelets. The plasmid pBrocSCR1-3CM7rgdcys was produced by restriction enzyme digestion of pBrocSCR1-3CM7 mutcys with ApaI and HindIII and purification of the large fragment. Two oligonucleotides were annealed in vitro and ligated into this fragment. The sequence of the inserted oligonucleotides was as follows. SEQ ID NO: 52 CGCACCGCAGTGCATCATCCCGAACAAAGATGGC CCGAGCGAAATTCTGCGTGGCGATTTTAGCA GCTGCTA and SEQ ID NO: 53: AGCTTAGCAGCTGCTAAAATCGCCACGCAGA ATTTCGCTCGGGCCATCTTTGTTCGGGATGAT GCACTGCGGTGCGGGCC. The amino acid sequence of the encoded protein is shown in SEQ ID NO: 54. The resulting colonies were analysed by restriction enzyme digestion and confirmed by DNA sequencing.

Example 11

Construction of Plasmid pBrocSCR1-3CM7T Cell Encoding CM7/T Cell

This construct consists of the sequence of CM7 fused at the C-terminus to an extension designed to target the protein to the T-cell receptor alpha subunit. The plasmid pBrocSCR1-3CM7T-cell was produced by restriction enzyme digestion of pBrocSCR1-3CM7 mutcys with ApaI and HindIII and purification of the large fragment. Two oligonucleotides were annealed in vitro and ligated into this fragment. The sequence of the inserted oligonucleotides was as follows. SEQ ID NO: 55 CGCACCGCAGTGCATCATCCCGAACAAAGCGGC GCCCAGCGTGATTGGCTTCCGTATTCTGCTG CTGAAAGTGGCGGGCTGATA and SEQ ID NO: 56: AGCTTATCAGCCCGCCACTTTCAGCAGCAGAA TACGGAAGCCAATCACGCTGGGCGCCGCTTTGT TCGGGATGATGCACTGCGGTGCGGGCC. The amino acid sequence of the encoded protein is shown in SEQ ID NO: 57. The resulting colonies were analysed by restriction enzyme digestion and confirmed by DNA sequencing.

Biological Activity (i) Anti-complement Activity Measured by the Classical Pathway-mediated Haemolysis of Sheep Erythrocytes Functional activity of complement inhibitors was assessed by measuring the inhibition of complement-mediated lysis of sheep erythrocytes sensitised with rabbit antibodies (Diamedix Corporation, Miami, USA). Human serum diluted 1:125 or 1:100 in 0.1 M Hepes/0.15 M NaCl/0.1% gelatin pH 7.4 was used as a source of complement. The serum was prepared from a pool of volunteers essentially as described in Dacie & Lewis, 1975. Briefly, blood was warmed to 37° C. for 5 minutes, the clot removed and the remaining serum clarified by centrifugation. The serum fraction was split into small aliquots and stored at −196° C. Aliquots were thawed as required and diluted in the Hepes buffer immediately before use.

Inhibition of complement-mediated lysis of sensitised sheep erythrocytes was measured using a standard haemolytic assay using a v-bottom microtitre plate format as follows:

50 μl of a range of concentrations of inhibitor (typically in the region of 0.1–100 nM) diluted in Hepes buffer were mixed with 50 μl of the diluted serum and 100 μl of prewarmed sensitised sheep erythrocytes and then incubated for 1 hour at 37° C. Samples were spun at 1600 rpm at ambient temperature for 3 minutes before transferring 150 μl of supernatant to flat bottom microtitre plates and determining the absorption at 410 nm. Maximum lysis (Amax) was determined by incubating serum with erythrocytes in the absence of any inhibitor. Background lysis (Ao) was determined by incubating erythrocytes in the absence of any serum or inhibitor. To check whether the inhibitor itself had any effect on lysis, erythrocytes were incubated with inhibitor alone; none of the compounds had any direct effect on lysis of the red blood cells. Inhibition was expressed as a fraction of the total cell lysis such that IH50 represents the concentration of inhibitor required to give 50% inhibition of lysis.

$$IH = \frac{A - Ao}{A\max - Ao}$$

where 0 is equivalent to complete inhibition and 1 equals no inhibition.

The CM7 protein product of Example 1 inhibited complement-mediated lysis of sensitised sheep red blood cells with an IH50 of approx. 6 nM. In a separate experiment, CM7 and CM7/cys preparations gave IH50 values of about 20–30 nM and they were experimentally indistinguishable from each other.

(ii) Anti-complement Activity Measured by Alternative Pathway-mediated Haemolysis of Guinea Pig Erythrocytes Functional activity of complement inhibitors was assessed by measuring the inhibition of complement mediated lysis of guinea pig erythrocytes essentially as described by Scesney, S. M. et al (1996) J. Immunol. 26 1729–1735. The assay is designed to be specific for the alternative pathway of complement activation. Human serum prepared from a pool of volunteers essentially as described in Dacie & Lewis, 1975 was used as the source of complement. Briefly, blood was warmed to 37° C. for 5 minutes, the clot removed and the remaining serum clarified by centrifugation. The serum fraction was split into small aliquots and stored at −196° C. Aliquots were thawed as required and diluted in 0.1 M Hepes/0.15 M NaCl/0.1% gelatin/8 mM EGTA/5 mM $MgCl_2$ pH 7.4 (buffer A) immediately before use. Guinea pig erythrocytes were prepared from guinea pig whole blood collected into EDTA-coated tubes as follows. The blood was spun at 1600 rpm for 5 min and the erythrocyte pellet washed 3 times with 0.1 M Hepes/0.15 M NaCl/0.1% gelatin pH 7.4 until the supernatant of the spin was essentially colourless. The erythrocytes were finally resuspended to the original volume of blood used and were stored at +4 degrees C. They were used within 2 weeks.

50 μl of a range of concentrations of inhibitor diluted in buffer A in a v-bottom microtitre plate were mixed with, first, 100 μl of serum that had been diluted 1:3 and second, 50 μl of guinea pig erythrocytes (diluted 1:49 in buffer A) and incubated for 1 hour at 37° C. The plate was spun at 1600 rpm for 3 minutes before transferring 150 μl of each supernatant to a flat bottom microtitre plate and determining the absorption at 405 nm, which reflects the amount of lysis in each test solution. Maximum lysis (Amax) was determined by incubating serum with erythrocytes in the absence of any inhibitor. Background lysis (Ao) was determined by incubating erythrocytes in the absence of any serum or inhibitor. To check whether the inhibitor itself had any effect on lysis, erythrocytes were incubated with inhibitor alone; none of the compounds had any direct effect on lysis of the red blood cells. The final dilution of serum used in the assay did absorb at 405 nm but the level of absorbance (approx 10% of Amax) was considered to have a neglible affect on the overall assay results and it was ignored in the calculations. Inhibition was expressed as a fraction of the total cell lysis such that IH50 represents the concentration of inhibitor required to give 50% inhibition of lysis.

% inhibition=1−[(A−Ao)/(Amax−Ao)]

CM7 final product similar to that described in Example 1 was assayed in the guinea pig haemolysis assay. In two separate assays the product inhibited haemolysis with IH50 values of 170 nM and 180 nM respectively.

(iii) Inhibition of Zymosan A-induced Activation of the Alternative Pathway by CM7

The alternative pathway of complement was activated with zymosan A, a complex carbohydrate from yeast (Sigma, catalogue number Z-4250). Zymosan A was made 50 mg/ml in Hepes buffer (0.1M Hepes/0.15M NaCl pH 7.4) and vortexed until a fine suspension had formed. Human serum was preincubated with different concentrations of complement inhibitor diluted in Hepes buffer for 15 mins at 37{SYMBOL 176/f "Symbol"}C using the volumes given below. Zymosan A was then vortexed for a few seconds each time before addition to the samples after which samples were incubated for a further 30 mins at 37{SYMBOL 176\f"Symbol"}C. The zymosan A was then spun down at approximately 11,000 g for 30 seconds at ambient temperature. 100 μl of supernatant were added to an equal volume of precipitating solution provided in the kit and assayed as described in the technical bulletin of Amersham with the C3a des Arg assay RIA kit purchased from Amersham International plc, U.K., (human complement C3a des Arg [$^{125}$I]assay, code RPA 518). In the C3a RIA Assay, activation of complement pathways can be followed by measuring the release of the anaphylatoxin, C3a and its breakdown product C3a des Arg. Both products can be measured using a competitive radio-immuno assay. Each sample was assayed in duplicate and a useful dilution was 1/100.

| Volumes of samples added | | | |
|---|---|---|---|
| | serum | inhibitor | Zymosan A |
| Normal Assay | 89 μl | 20 μl | 21 μl |

The data were computed essentially as described in the Amersham technical bulletin with the exception that the standard curve was not used and data were calculated only as B/Bo.

Controls included maximum activation (A) i.e. serum+ zymosan A only, background activation (B) i.e. serum+ buffer only and background activation in the presence of inhibitor (C) i.e. serum+inhibitor only. D is the value of activation of serum in the presence of inhibitor and zymosan A, These values could then be used to determine the % inhibition at each inhibitor concentration using the following formula I. Note that the formula looks unusual because of the nature of the assay, in particular that because the assay is a competition assay all factors are inversed eg. maximum activation actually gives the lowest counts in the assay.

Formula I: $\dfrac{D-A}{C-A} \times 100$

The IC50 is defined as the concentration of inhibitor required to reduce maximum activation by 50%. Using the data generated experimentally and reproduced in the table below, the IC50 for CM 7 of Example 1 was about 1 μM and was indistinguishable from that of SCR1-3 prepared as described in WO94/00571

| μM | SCR1–3 | CM7 |
|---|---|---|
| 21.5 | | 106 |
| 15.4 | 87 | |
| 5.4 | | 59 |
| 3.8 | 65 | |
| 1.35 | | 54 |
| 0.96 | 43 | |
| 0.34 | | 15 |
| 0.24 | 17 | |
| 0.084 | | 7 |
| 0.06 | 6 | |
| 0.021 | | -2 |
| 0.015 | -3 | |

It is claimed:

1. A soluble polypeptide comprising, in sequence, short consensus repeats (SCR) 1, 2 and 3 of long homologous repeat A (LHR-A) (SEQ ID NO: 59) with a substitution of at least one SCR native amino acid, wherein the soluble polypeptide is CM7 (SEQ ID NO. 1).

2. The soluble polypeptide of claim 1, wherein the soluble polypeptide further comprises a C-terminal cysteine (SEQ ID NO. 31).

* * * * *

SEQUENCE LISTING (1) GENERAL INFORMATION:

(iii) NUMBER OF SEQUENCES: 64

(2) INFORMATION FOR SEQ ID NO: 1:

(i) SEQUENCE CHARACTERISTICS:
      (A) LENGTH: 197 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 1:

```
Met Gln Cys Asn Ala Pro Glu Trp Leu Pro Phe Ala Arg Pro Thr Asn
1               5                   10                  15

Leu Thr Asp Glu Phe Glu Phe Pro Ile Gly Thr Tyr Leu Asn Tyr Glu
                20                  25                  30

Cys Arg Pro Gly Tyr Ser Gly Arg Pro Phe Ser Ile Ile Cys Leu Lys
            35                  40                  45

Asn Ser Val Trp Thr Gly Ala Lys Asp Arg Cys Arg Arg Lys Ser Cys
    50                  55                  60

Arg Asn Pro Pro Asp Pro Val Asn Gly Met Val His Val Ile Lys Gly
65                  70                  75                  80

Ile Gln Phe Gly Ser Gln Ile Lys Tyr Ser Cys Thr Lys Gly Tyr Arg
                85                  90                  95

Leu Ile Gly Ser Ser Ser Ala Thr Cys Ile Ile Ser Gly Asp Thr Val
                100                 105                 110

Ile Trp Asp Asn Glu Thr Pro Ile Cys Asp Arg Ile Pro Cys Gly Leu
            115                 120                 125

Pro Pro Thr Ile Ala Asn Gly Asp Phe Thr Ser Ile Ser Arg Glu Tyr
            130                 135                 140

Phe His Tyr Gly Ser Val Val Thr Tyr His Cys Asn Leu Gly Ser Arg
145                 150                 155                 160

Gly Lys Lys Val Phe Glu Leu Val Gly Glu Pro Ser Ile Tyr Cys Thr
                165                 170                 175

Ser Lys Asp Asp Gln Val Gly Ile Trp Ser Gly Pro Ala Pro Gln Cys
            180                 185                 190
```

Ile Ile Pro Asn Lys
      195

(2) INFORMATION FOR SEQ ID NO: 2:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

| | | | | | |
|---|---|---|---|---|---|
| ATGCAGTGCA | ACGCTCCGGA | ATGGCTGCCG | TTCGCGCGCC | CGACCAACCT | GACTGATGAA | 60
| TTTGAGTTCC | CGATCGGTAC | CTACCTGAAC | TACGAATGCC | GCCCGGGTTA | TAGCGGCCGC | 120
| CCGTTTTCTA | TCATCTGCCT | GAAAAACTCT | GTCTGGACTG | GTGCTAAGGA | CCGTTGCCGA | 180
| CGTAAATCTT | GTCGTAATCC | GCCAGATCCG | GTTAACGGCA | TGGTGCATGT | GATCAAAGGC | 240
| ATCCAGTTCG | GTTCCCAAAT | TAAATATTCT | TGTACTAAAG | GTTACCGTCT | GATTGGTTCC | 300
| TCCAGCGCTA | CATGCATCAT | CTCTGGTGAT | ACTGTCATTT | GGGATAATGA | AACACCGATT | 360
| TGTGACCGAA | TTCCGTGTGG | TCTGCCGCCG | ACCATCGCCA | ACGGTGATTT | CACCTCTATC | 420
| AGTCGCGAGT | ATTTTCACTA | TGGTTCTGTG | GTGACCTACC | ACTGCAATCT | GGGTAGCCGT | 480
| GGTAAAAAGG | TGTTTGAGCT | CGTGGGTGAG | CCGTCCATCT | ACTGCACTAG | CAAAGACGAT | 540
| CAAGTGGGCA | TCTGGAGCGG | CCCGGCACCG | CAGTGCATCA | TCCCGAACAA | A | 591

(2) INFORMATION FOR SEQ ID NO: 3:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

CGACCATCGC CAACGGTGAT TTCACCTCTA TCAGTCGCGA GTATTTTCAC          50

(2) INFORMATION FOR SEQ ID NO: 4:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GTGAAAATAC TCGCGACTGA TAGAGGTGAA ATCACCGTTG GCGATGGTCG          50

(2) INFORMATION FOR SEQ ID NO: 5:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
GACCTACCAC TGCAATCTGG GTAGCCGTGG TAAAAAGGTG TTTGAGC                    47

(2) INFORMATION FOR SEQ ID NO: 6:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

GCTCAAACAC CTTTTTACCA CGGCTACCCA GATTGCAGTG GTAGGTC                    47

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GCACTAGCAA AGACGATCAA GTGGG                                            25

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

CCCACTTGAT CGTCTTTGCT AGTGC                                            25

(2) INFORMATION FOR SEQ ID NO: 9:

(i) SEQUENCE CHARACTERISTICS:
        (A) LENGTH: 197 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

Met Gln Cys Asn Ala Pro Glu Trp Leu Pro Phe Ala Arg Pro Thr Asn
1               5                   10                  15

Leu Thr Asp Glu Phe Glu Phe Pro Ile Gly Thr Tyr Leu Asn Tyr Glu
            20                  25                  30

Cys Arg Pro Gly Tyr Ser Gly Arg Pro Phe Ser Ile Ile Cys Leu Lys
        35                  40                  45

Asn Ser Val Trp Thr Gly Ala Lys Asp Arg Cys Arg Arg Lys Ser Cys
    50                  55                  60

Arg Asn Pro Pro Asp Pro Val Asn Gly Met Val His Val Ile Lys Gly
65                  70                  75                  80

Ile Gln Phe Gly Ser Gln Ile Lys Tyr Ser Cys Thr Lys Gly Tyr Arg
            85                  90                  95
```

```
Leu Ile Gly Ser Ser Ala Thr Cys Ile Ser Gly Asp Thr Val
            100                 105                 110

Ile Trp Asp Asn Glu Thr Pro Ile Cys Asp Arg Ile Pro Cys Gly Leu
        115                 120                 125

Pro Pro Thr Ile Ala Asn Gly Asp Phe Thr Ser Ile Ser Arg Glu Tyr
        130                 135                 140

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
            180                 185                 190

Ile Ile Pro Asn Lys
            195
```

(2) INFORMATION FOR SEQ ID NO: 10:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
ATGCAGTGCA ACGCTCCGGA ATGGCTGCCG TTCGCGCGCC CGACCAACCT GACTGATGAA      60
TTTGAGTTCC CGATCGGTAC CTACCTGAAC TACGAATGCC GCCCGGGTTA TAGCGGCCGC     120
CCGTTTTCTA TCATCTGCCT GAAAAACTCT GTCTGGACTG GTGCTAAGGA CCGTTGCCGA     180
CGTAAATCTT GTCGTAATCC GCCAGATCCG GTTAACGGCA TGGTGCATGT GATCAAAGGC     240
ATCCAGTTCG GTTCCCAAAT TAAATATTCT TGTACTAAAG GTTACCGTCT GATTGGTTCC     300
TCCAGCGCTA CATGCATCAT CTCTGGTGAT ACTGTCATTT GGGATAATGA ACACCGATT      360
TGTGACCGAA TTCCGTGTGG TCTGCCGCCG ACCATCGCCA ACGGTGATTT CACCTCTATC     420
AGTCGCGAGT ATTTTCACTA TGGTTCTGTG GTGACCTACC GCTGCAATCC GGGTAGCGGT     480
GGTCGTAAGG TGTTTGAGCT CGTGGGTGAG CCGTCCATCT ACTGCACTAG TAATGACGAT     540
CAAGTGGGCA TCTGGAGCGG CCCGGCACCG CAGTGCATCA TCCCGAACAA A              591
```

(2) INFORMATION FOR SEQ ID NO: 11:

(i) SEQUENCE CHARACTERISTICS:
        (A) LENGTH: 197 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 11:

```
Met Gln Cys Asn Ala Pro Glu Trp Leu Pro Phe Ala Arg Pro Thr Asn
1               5                   10                  15

Leu Thr Asp Glu Phe Glu Phe Pro Ile Gly Thr Tyr Leu Asn Tyr Glu
            20                  25                  30

Cys Arg Pro Gly Tyr Ser Gly Arg Pro Phe Ser Ile Ile Cys Leu Lys
            35                  40                  45

Asn Ser Val Trp Thr Gly Ala Lys Asp Arg Cys Arg Arg Lys Ser Cys
        50                  55                  60
```

```
Arg Asn Pro Pro Asp Pro Val Asn Gly Met Val His Val Ile Lys Gly
 65                  70                  75                  80

Ile Gln Phe Gly Ser Gln Ile Lys Tyr Ser Cys Thr Lys Gly Tyr Arg
                 85                  90                  95

Leu Ile Gly Ser Ser Ser Ala Thr Cys Ile Ile Ser Gly Asp Thr Val
            100                 105                 110

Ile Trp Asp Asn Glu Thr Pro Ile Cys Asp Arg Ile Pro Cys Gly Leu
        115                 120                 125

Pro Pro Thr Ile Thr Asn Gly Asp Phe Ile Ser Thr Asn Arg Glu Asn
    130                 135                 140

Phe His Tyr Gly Ser Val Val Thr Tyr His Cys Asn Leu Gly Ser Arg
145                 150                 155                 160

Gly Lys Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
            180                 185                 190

Ile Ile Pro Asn Lys
        195

(2) INFORMATION FOR SEQ ID NO: 12:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

ATGCAGTGCA ACGCTCCGGA ATGGCTGCCG TTCGCGCGCC CGACCAACCT GACTGATGAA     60

TTTGAGTTCC CGATCGGTAC CTACCTGAAC TACGAATGCC GCCCGGGTTA TAGCGGCCGC    120

CCGTTTTCTA TCATCTGCCT GAAAAACTCT GTCTGGACTG GTGCTAAGGA CCGTTGCCGA    180

CGTAAATCTT GTCGTAATCC GCCAGATCCG GTTAACGGCA TGGTGCATGT GATCAAAGGC    240

ATCCAGTTCG GTTCCCAAAT TAAATATTCT TGTACTAAAG GTTACCGTCT GATTGGTTCC    300

TCCAGCGCTA CATGCATCAT CTCTGGTGAT ACTGTCATTT GGGATAATGA AACACCGATT    360

TGTGACCGAA TTCCGTGTGG TCTGCCGCCG ACCATCACCA ACGGTGATTT CATCTCTACC    420

AATCGCGAGA ATTTTCACTA TGGTTCTGTG GTGACCTACC ACTGCAATCT GGGTAGCCGT    480

GGTAAAAAGG TGTTTGAGCT CGTGGGTGAG CCGTCCATCT ACTGCACTAG TAATGACGAT    540

CAAGTGGGCA TCTGGAGCGG CCCGGCACCG CAGTGCATCA TCCCGAACAA A             591

(2) INFORMATION FOR SEQ ID NO: 13:

(i) SEQUENCE CHARACTERISTICS:
        (A) LENGTH: 197 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 13:

Met Gln Cys Asn Ala Pro Glu Trp Leu Pro Phe Ala Arg Pro Thr Asn
  1               5                  10                  15

Leu Thr Asp Glu Phe Glu Phe Pro Ile Gly Thr Tyr Leu Asn Tyr Glu
             20                  25                  30
```

```
Cys Arg Pro Gly Tyr Ser Gly Arg Pro Phe Ser Ile Ile Cys Leu Lys
        35                  40                  45

Asn Ser Val Trp Thr Gly Ala Lys Asp Arg Cys Arg Arg Lys Ser Cys
    50                  55                  60

Arg Asn Pro Pro Asp Pro Val Asn Gly Met Val His Val Ile Lys Gly
 65              70                  75                  80

Ile Gln Phe Gly Ser Gln Ile Lys Tyr Ser Cys Thr Lys Gly Tyr Arg
                85                  90                  95

Leu Ile Gly Ser Ser Ser Ala Thr Cys Ile Ile Ser Gly Asp Thr Val
               100                 105                 110

Ile Trp Asp Asn Glu Thr Pro Ile Cys Asp Arg Ile Pro Cys Gly Leu
       115                 120                 125

Pro Pro Thr Ile Thr Asn Gly Asp Phe Ile Ser Thr Asn Arg Glu Asn
130                 135                 140

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Lys Asp Asp Gln Val Gly Ile Trp Ser Gly Pro Ala Pro Gln Cys
               180                 185                 190

Ile Ile Pro Asn Lys
               195

(2) INFORMATION FOR SEQ ID NO: 14:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

ATGCAGTGCA ACGCTCCGGA ATGGCTGCCG TTCGCGCGCC CGACCAACCT GACTGATGAA      60

TTTGAGTTCC CGATCGGTAC CTACCTGAAC TACGAATGCC GCCCGGGTTA TAGCGGCCG      120

CCGTTTTCTA TCATCTGCCT GAAAAACTCT GTCTGGACTG GTGCTAAGGA CCGTTGCCG      180

CGTAAATCTT GTCGTAATCC GCCAGATCCG GTTAACGGCA TGGTGCATGT GATCAAAGG      240

ATCCAGTTCG GTTCCCAAAT TAAATATTCT TGTACTAAAG GTTACCGTCT GATTGGTTC      300

TCCAGCGCTA CATGCATCAT CTCTGGTGAT ACTGTCATTT GGGATAATGA AACACCGAT      360

TGTGACCGAA TTCCGTGTGG TCTGCCGCCG ACCATCACCA ACGGTGATTT CATCTCTAC      420

AATCGCGAGA ATTTTCACTA TGGTTCTGTG GTGACCTACC GCTGCAATCC GGGTAGCGG      480

GGTCGTAAGG TGTTTGAGCT CGTGGGTGAG CCGTCCATCT ACTGCACTAG CAAAGACGA      540

CAAGTGGGCA TCTGGAGCGG CCCGGCACCG CAGTGCATCA TCCCGAACAA A              591

(2) INFORMATION FOR SEQ ID NO: 15:

(i) SEQUENCE CHARACTERISTICS:
        (A) LENGTH: 197 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 15:
```

```
Met Gln Cys Asn Ala Pro Glu Trp Leu Pro Phe Ala Arg Pro Thr As
1               5                   10                  15

Leu Thr Asp Glu Phe Glu Phe Pro Ile Gly Thr Tyr Leu Asn Tyr Gl
                20              25                  30

Cys Arg Pro Gly Tyr Ser Gly Arg Pro Phe Ser Ile Ile Cys Leu Ly
                35              40                  45

Asn Ser Val Trp Thr Gly Ala Lys Asp Arg Cys Arg Arg Lys Ser Cy
    50              55                  60

Arg Asn Pro Pro Asp Pro Val Asn Gly Met Val His Val Ile Lys Gl
65              70                  75                  80

Ile Gln Phe Gly Ser Gln Ile Lys Tyr Ser Cys Thr Lys Gly Tyr Ar
                85                  90                  95

Leu Ile Gly Ser Ser Ser Ala Thr Cys Ile Ile Ser Gly Asp Thr Va
                100             105                 110

Ile Trp Asp Asn Glu Thr Pro Ile Cys Asp Arg Ile Pro Cys Gly Le
            115                 120                 125

Pro Pro Thr Ile Ala Asn Gly Asp Phe Thr Ser Ile Ser Arg Glu Ty
130             135                 140

Phe His Tyr Gly Ser Val Val Thr Tyr Arg Cys Asn Pro Gly Ser Gl
145             150                 155                 160

Gly Arg Lys Val Phe Glu Leu Val Gly Glu Pro Ser Ile Tyr Cys Th
                165                 170                 175

Ser Lys Asp Asp Gln Val Gly Ile Trp Ser Gly Pro Ala Pro Gln Cy
                180                 185                 190

Ile Ile Pro Asn Lys
        195

(2) INFORMATION FOR SEQ ID NO: 16:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

ATGCAGTGCA ACGCTCCGGA ATGGCTGCCG TTCGCGCGCC CGACCAACCT GACTGATGAA      60

TTTGAGTTCC CGATCGGTAC CTACCTGAAC TACGAATGCC GCCCGGGTTA TAGCGGCCG      120

CCGTTTTCTA TCATCTGCCT GAAAAACTCT GTCTGGACTG GTGCTAAGGA CCGTTGCCG      180

CGTAAATCTT GTCGTAATCC GCCAGATCCG GTTAACGGCA TGGTGCATGT GATCAAAGG      240

ATCCAGTTCG GTTCCCAAAT TAAATATTCT TGTACTAAAG GTTACCGTCT GATTGGTTC      300

TCCAGCGCTA CATGCATCAT CTCTGGTGAT ACTGTCATTT GGGATAATGA AACACCGAT      360

TGTGACCGAA TTCCGTGTGG TCTGCCGCCA ACCATCGCCA ACGGTGATTT CACCTCTAT      420

AGTCGCGAGT ATTTTCACTA TGGTTCTGTG GTGACCTACC GCTGCAATCC GGGTAGCGG      480

GGTCGTAAGG TGTTTGAGCT CGTGGGTGAG CCGTCCATCT ACTGCACTAG CAAAGACGA      540

CAAGTGGGCA TCTGGAGCGG CCCGGCACCG CAGTGCATCA TCCCGAACAA A             591

(2) INFORMATION FOR SEQ ID NO: 17:

(i) SEQUENCE CHARACTERISTICS:
        (A) LENGTH: 197 amino acids
        (B) TYPE: amino acid
        (C) STRANDEDNESS: <Unknown>
```

(D) TOPOLOGY: linear (ii) MOLECULE TYPE: peptide (xi) SEQUENCE DESCRIPTION: SEQ ID NO: 17:

```
Met Gln Cys Asn Ala Pro Glu Trp Leu Pro Phe Ala Arg Pro Thr As
1               5                   10                  15
Leu Thr Asp Glu Phe Glu Phe Pro Ile Gly Thr Tyr Leu Asn Tyr Gl
                20                  25                  30
Cys Arg Pro Gly Tyr Ser Gly Arg Pro Phe Ser Ile Ile Cys Leu Ly
            35                  40                  45
Asn Ser Val Trp Thr Gly Ala Lys Asp Arg Cys Arg Arg Lys Ser Cy
        50                  55                  60
Arg Asn Pro Pro Asp Pro Val Asn Gly Met Val His Val Ile Lys Gl
65                  70                  75                  80
Ile Gln Phe Gly Ser Gln Ile Lys Tyr Ser Cys Thr Lys Gly Tyr Ar
                85                  90                  95
Leu Ile Gly Ser Ser Ser Ala Thr Cys Ile Ile Ser Gly Asp Thr Va
                100                 105                 110
Ile Trp Asp Asn Glu Thr Pro Ile Cys Asp Arg Ile Pro Cys Gly Le
            115                 120                 125
Pro Pro Thr Ile Thr Asn Gly Asp Phe Ile Ser Thr Asn Arg Glu As
        130                 135                 140
Phe His Tyr Gly Ser Val Val Thr Tyr His Cys Asn Leu Gly Ser Ar
145                 150                 155                 160
Gly Lys Lys Val Phe Glu Leu Val Gly Glu Pro Ser Ile Tyr Cys Th
                165                 170                 175
Ser Lys Asp Asp Gln Val Gly Ile Trp Ser Gly Pro Ala Pro Gln Cy
                180                 185                 190
Ile Ile Pro Asn Lys
            195
```

(2) INFORMATION FOR SEQ ID NO: 18:

(i) SEQUENCE CHARACTERISTICS:
(A) LENGTH: 591 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 18:

```
ATGCAGTGCA ACGCTCCGGA ATGGCTGCCG TTCGCGCGCC CGACCAACCT GACTGATGAA      60
TTTGAGTTCC CGATCGGTAC CTACCTGAAC TACGAATGCC GCCCGGGTTA TAGCGGCCG      120
CCGTTTTCTA TCATCTGCCT GAAAAACTCT GTCTGGACTG GTGCTAAGGA CCGTTGCCG      180
CGTAAATCTT GTCGTAATCC GCCAGATCCG GTTAACGGCA TGGTGCATGT GATCAAAGG      240
ATCCAGTTCG GTTCCCAAAT TAAATATTCT TGTACTAAAG GTTACCGTCT GATTGGTTC      300
TCCAGCGCTA CATGCATCAT CTCTGGTGAT ACTGTCATTT GGGATAATGA ACACCGAT       360
TGTGACCGAA TTCCGTGTGG TCTGCCGCCG ACCATCACCA ACGGTGATTT CATCTCTAC      420
AATCGCGAGA ATTTTCACTA TGGTTCTGTG GTGACCTACC ACTGCAATCT GGGTAGCCG      480
GGTAAAAAGG TGTTTGAGCT CGTGGGTGAG CCGTCCATCT ACTGCACTAG CAAAGACGA      540
CAAGTGGGCA TCTGGAGCGG CCCGGCACCG CAGTGCATCA TCCCGAACAA A              591
```

(2) INFORMATION FOR SEQ ID NO: 19:

(i) SEQUENCE CHARACTERISTICS:
        (A) LENGTH: 76 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 19:

```
Met Arg Ile Pro Cys Gly Leu Pro Pro Thr Ile Ala Asn Gly Asp Ph
1               5                   10                  15

Thr Ser Ile Ser Arg Glu Tyr Phe His Tyr Gly Ser Val Val Thr Ty
                20                  25                  30

Arg Cys Asn Pro Gly Ser Gly Gly Arg Lys Val Phe Glu Leu Val Gl
                35                  40                  45

Glu Pro Ser Ile Tyr Cys Thr Ser Asn Asp Asp Gln Val Gly Ile Tr
        50                  55                  60

Ser Gly Pro Ala Pro Gln Cys Ile Ile Pro Asn Lys
65                  70                  75
```

(2) INFORMATION FOR SEQ ID NO: 20:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

```
ATGCGAATTC CGTGTGGTCT GCCGCCGACC ATCGCCAACG GTGATTTCAC CTCTATCAGT      60

CGCGAGTATT TTCACTATGG TTCTGTGGTG ACCTACCGCT GCAATCCGGG TAGCGGTGG      120

CGTAAGGTGT TTGAGCTCGT GGGTGAGCCG TCCATCTACT GCACTAGTAA TGACGATCA      180

GTGGGCATCT GGAGCGGCCC GGCACCGCAG TGCATCATCC CGAACAAA                  228
```

(2) INFORMATION FOR SEQ ID NO: 21:

(i) SEQUENCE CHARACTERISTICS:
        (A) LENGTH: 76 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 21:

```
Met Arg Ile Pro Cys Gly Leu Pro Pro Thr Ile Thr Asn Gly Asp Ph
1               5                   10                  15

Ile Ser Thr Asn Arg Glu Asn Phe His Tyr Gly Ser Val Val Thr Ty
                20                  25                  30

His Cys Asn Leu Gly Ser Arg Gly Lys Lys Val Phe Glu Leu Val Gl
                35                  40                  45

Glu Pro Ser Ile Tyr Cys Thr Ser Asn Asp Asp Gln Val Gly Ile Tr
        50                  55                  60

Ser Gly Pro Ala Pro Gln Cys Ile Ile Pro Asn Lys
65                  70                  75
```

(2) INFORMATION FOR SEQ ID NO: 22:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

ATGCGAATTC CGTGTGGTCT GCCGCCGACC ATCACCAACG GTGATTTCAT CTCTACCAAT      60

CGCGAGAATT TTCACTATGG TTCTGTGGTG ACCTACCACT GCAATCTGGG TAGCCGTGG       120

AAAAAGGTGT TGAGCTCGT GGGTGAGCCG TCCATCTACT GCACTAGTAA TGACGATCA        180

GTGGGCATCT GGAGCGGCCC GGCACCGCAG TGCATCATCC CGAACAAA                   228

(2) INFORMATION FOR SEQ ID NO: 23:

(i) SEQUENCE CHARACTERISTICS:
        (A) LENGTH: 76 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 23:

Met Arg Ile Pro Cys Gly Leu Pro Pro Thr Ile Ala Asn Gly Asp Ph
1               5                   10                  15

Thr Ser Ile Ser Arg Glu Tyr Phe His Tyr Gly Ser Val Val Thr Ty
                20                  25                  30

Arg Cys Asn Pro Gly Ser Gly Gly Arg Lys Val Phe Glu Leu Val Gl
            35                  40                  45

Glu Pro Ser Ile Tyr Cys Thr Ser Lys Asp Asp Gln Val Gly Ile Tr
        50                  55                  60

Ser Gly Pro Ala Pro Gln Cys Ile Ile Pro Asn Lys
65                  70                  75

(2) INFORMATION FOR SEQ ID NO: 24:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

ATGCGAATTC CGTGTGGTCT GCCGCCGACC ATCACCAACG GTGATTTCAT CTCTACCAAT      60

CGCGAGAATT TTCACTATGG TTCTGTGGTG ACCTACCGCT GCAATCCGGG TAGCGGTGG       120

CGTAAGGTGT TGAGCTCGT GGGTGAGCCG TCCATCTACT GCACTAGCAA AGACGATCA        180

GTGGGCATCT GGAGCGGCCC GGCACCGCAG TGCATCATCC CGAACAAA                   228

(2) INFORMATION FOR SEQ ID NO: 25:

(i) SEQUENCE CHARACTERISTICS:
        (A) LENGTH: 76 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 25:

Met Arg Ile Pro Cys Gly Leu Pro Pro Thr Ile Ala Asn Gly Asp Ph
1               5                   10                  15

Thr Ser Ile Ser Arg Glu Tyr Phe His Tyr Gly Ser Val Val Thr Ty
                20                  25                  30

Arg Cys Asn Pro Gly Ser Gly Gly Arg Lys Val Phe Glu Leu Val Gl
                35                  40                  45

Glu Pro Ser Ile Tyr Cys Thr Ser Lys Asp Asp Gln Val Gly Ile Tr
    50                  55                  60

Ser Gly Pro Ala Pro Gln Cys Ile Ile Pro Asn Lys
65              70                  75

(2) INFORMATION FOR SEQ ID NO: 26:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

```
ATGCGAATTC CGTGTGGTCT GCCGCCGACC ATCGCCAACG GTGATTTCAC CTCTATCAGT      60
CGCGAGTATT TTCACTATGG TTCTGTGGTG ACCTACCGCT GCAATCCGGG TAGCGGTGG      120
CGTAAGGTGT TTGAGCTCGT GGGTGAGCCG TCCATCTACT GCACTAGCAA AGACGATCA      180
GTGGGCATCT GGAGCGGCCC GGCACCGCAG TGCATCATCC CGAACAAA                  228
```

(2) INFORMATION FOR SEQ ID NO: 27:

(i) SEQUENCE CHARACTERISTICS:
        (A) LENGTH: 76 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 27:

Met Arg Ile Pro Cys Gly Leu Pro Pro Thr Ile Thr Asn Gly Asp Ph
1               5                   10                  15

Ile Ser Thr Asn Arg Glu Asn Phe His Tyr Gly Ser Val Val Thr Ty
                20                  25                  30

His Cys Asn Leu Gly Ser Arg Gly Lys Lys Val Phe Glu Leu Val Gl
                35                  40                  45

Glu Pro Ser Ile Tyr Cys Thr Ser Lys Asp Asp Gln Val Gly Ile Tr
    50                  55                  60

Ser Gly Pro Ala Pro Gln Cys Ile Ile Pro Asn Lys
65              70                  75

(2) INFORMATION FOR SEQ ID NO: 28:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

```
ATGCGAATTC CGTGTGGTCT GCCGCCGACC ATCACCAACG GTGATTTCAT CTCTACCAAT      60
```

```
CGCGAGAATT TTCACTATGG TTCTGTGGTG ACCTACCACT GCAATCTGGG TAGCCGTGG      120

AAAAAGGTGT TTGAGCTCGT GGGTGAGCCG TCCATCTACT GCACTAGCAA AGACGATCA      180

GTGGGCATCT GGAGCGGCCC GGCACCGCAG TGCATCATCC CGAACAAA                  228

(2) INFORMATION FOR SEQ ID NO: 29:

(i) SEQUENCE CHARACTERISTICS:
        (A) LENGTH: 76 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 29:

Met Arg Ile Pro Cys Gly Leu Pro Pro Thr Ile Ala Asn Gly Asp Ph
1               5                   10                  15

Thr Ser Ile Ser Arg Glu Tyr Phe His Tyr Gly Ser Val Val Thr Ty
            20                  25                  30

His Cys Asn Leu Gly Ser Arg Gly Lys Lys Val Phe Glu Leu Val Gl
        35                  40                  45

Glu Pro Ser Ile Tyr Cys Thr Ser Lys Asp Asp Gln Val Gly Ile Tr
    50                  55                  60

Ser Gly Pro Ala Pro Gln Cys Ile Ile Pro Asn Lys
65                  70                  75

(2) INFORMATION FOR SEQ ID NO: 30:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

ATGCGAATTC CGTGTGGTCT GCCGCCGACC ATCGCCAACG GTGATTTCAC CTCTATCAGT      60

CGCGAGTATT TTCACTATGG TTCTGTGGTG ACCTACCACT GCAATCTGGG TAGCCGTGG      120

AAAAAGGTGT TTGAGCTCGT GGGTGAGCCG TCCATCTACT GCACTAGCAA AGACGATCA      180

GTGGGCATCT GGAGCGGCCC GGCACCGCAG TGCATCATCC CGAACAAA                  228

(2) INFORMATION FOR SEQ ID NO: 31:

(i) SEQUENCE CHARACTERISTICS:
        (A) LENGTH: 198 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 31:

Met Gln Cys Asn Ala Pro Glu Trp Leu Pro Phe Ala Arg Pro Thr As
1               5                   10                  15

Leu Thr Asp Glu Phe Glu Phe Pro Ile Gly Thr Tyr Leu Asn Tyr Gl
            20                  25                  30

Cys Arg Pro Gly Tyr Ser Gly Arg Pro Phe Ser Ile Ile Cys Leu Ly
        35                  40                  45

Asn Ser Val Trp Thr Gly Ala Lys Asp Arg Cys Arg Arg Lys Ser Cy
```

```
                50                  55                  60
Arg Asn Pro Pro Asp Pro Val Asn Gly Met Val His Val Ile Lys Gl
 65                  70                  75                  80

Ile Gln Phe Gly Ser Gln Ile Lys Tyr Ser Cys Thr Lys Gly Tyr Ar
                 85                  90                  95

Leu Ile Gly Ser Ser Ser Ala Thr Cys Ile Ile Ser Gly Asp Thr Va
                100                 105                 110

Ile Trp Asp Asn Glu Thr Pro Ile Cys Asp Arg Ile Pro Cys Gly Le
            115                 120                 125

Pro Pro Thr Ile Ala Asn Gly Asp Phe Thr Ser Ile Ser Arg Glu Ty
130                 135                 140

Phe His Tyr Gly Ser Val Val Thr Tyr His Cys Asn Leu Gly Ser Ar
145                 150                 155                 160

Gly Lys Lys Val Phe Glu Leu Val Gly Glu Pro Ser Ile Tyr Cys Th
                165                 170                 175

Ser Lys Asp Asp Gln Val Gly Ile Trp Ser Gly Pro Ala Pro Gln Cy
            180                 185                 190

Ile Ile Pro Asn Lys Cys
            195
```

(2) INFORMATION FOR SEQ ID NO: 32:

(i) SEQUENCE CHARACTERISTICS:
    (A) LENGTH: 53 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 32:

CTGGAGCGGG CCCGCACCGC AGTGCATCAT CCCGAACAAA TGCTAATAAA AGC  53

(2) INFORMATION FOR SEQ ID NO: 33:

(i) SEQUENCE CHARACTERISTICS:
    (A) LENGTH: 53 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 33:

GCTTTTATTA GCATTTGTTC GGGATGATGC ACTGCGGTGC GGGCCCGCTC CAG  53

(2) INFORMATION FOR SEQ ID NO: 34:

(i) SEQUENCE CHARACTERISTICS:
    (A) LENGTH: 215 amino acids
    (B) TYPE: amino acid
    (C) STRANDEDNESS: <Unknown>
    (D) TOPOLOGY: linear (ii) MOLECULE TYPE: peptide (xi) SEQUENCE DESCRIPTION: SEQ ID NO: 34:

```
Met Gln Cys Asn Ala Pro Glu Trp Leu Pro Phe Ala Arg Pro Thr As
 1               5                  10                  15

Leu Thr Asp Glu Phe Glu Phe Pro Ile Gly Thr Tyr Leu Asn Tyr Gl
                 20                  25                  30

Cys Arg Pro Gly Tyr Ser Gly Arg Pro Phe Ser Ile Ile Cys Leu Ly
```

```
                    35                  40                  45
Asn Ser Val Trp Thr Gly Ala Lys Asp Arg Cys Arg Arg Lys Ser Cy
 50                      55                  60

Arg Asn Pro Pro Asp Pro Val Asn Gly Met Val His Val Ile Lys Gl
 65                  70                  75                  80

Ile Gln Phe Gly Ser Gln Ile Lys Tyr Ser Cys Thr Lys Gly Tyr Ar
                 85                  90                  95

Leu Ile Gly Ser Ser Ala Thr Cys Ile Ile Ser Gly Asp Thr Va
                100                 105                 110

Ile Trp Asp Asn Glu Thr Pro Ile Cys Asp Arg Ile Pro Cys Gly Le
            115                 120                 125

Pro Pro Thr Ile Ala Asn Gly Asp Phe Thr Ser Ile Ser Arg Glu Ty
130                 135                 140

Phe His Tyr Gly Ser Val Val Thr Tyr His Cys Asn Leu Gly Ser Ar
145                 150                 155                 160

Gly Lys Lys Val Phe Glu Leu Val Gly Glu Pro Ser Ile Tyr Cys Th
                165                 170                 175

Ser Lys Asp Asp Gln Val Gly Ile Trp Ser Gly Pro Ala Pro Gln Cy
            180                 185                 190

Ile Ile Pro Asn Lys Cys Cys Asp Gly Pro Lys Lys Lys Lys Lys Ly
        195                 200                 205

Ser Pro Ser Lys Ser Ser Gly
210                 215

(2) INFORMATION FOR SEQ ID NO: 35:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 35:

Gly Ser Ser Lys Ser Pro Ser Lys Lys Lys Lys Lys Lys Pro Gly As
 1               5                  10                  15

Cys (2) INFORMATION FOR SEQ ID NO: 36:

(i) SEQUENCE CHARACTERISTICS:
        (A) LENGTH: 198 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 36:

Met Gln Cys Asn Val Pro Glu Trp Leu Pro Phe Ala Arg Pro Thr As
 1               5                  10                  15

Leu Thr Asp Asp Phe Glu Phe Pro Ile Gly Thr Tyr Leu Asn Tyr Gl
            20                  25                  30

Cys Arg Pro Gly Tyr Ser Gly Arg Pro Phe Ser Ile Ile Cys Leu Ly
            35                  40                  45

Asn Ser Val Trp Thr Ser Ala Lys Asp Lys Cys Lys Arg Lys Ser Cy
 50                  55                  60

Arg Asn Pro Pro Asp Pro Val Asn Gly Met Ala His Val Ile Lys As
```

```
             65                  70                  75                  80
Ile Gln Phe Arg Ser Gln Ile Lys Tyr Ser Cys Pro Lys Gly Tyr Ar
                 85                  90                  95

Leu Ile Gly Ser Ser Ser Ala Thr Cys Ile Ile Ser Gly Asn Thr Va
                100                 105                 110

Ile Trp Asp Asn Lys Thr Pro Val Cys Asp Arg Ile Ile Cys Gly Le
            115                 120                 125

Pro Pro Thr Ile Ala Asn Gly Asp Phe Thr Ser Ile Ser Arg Glu Ty
        130                 135                 140

Phe His Tyr Gly Ser Val Val Thr Tyr His Cys Asn Leu Gly Ser Ar
145                 150                 155                 160

Gly Lys Lys Val Phe Glu Leu Val Gly Glu Pro Ser Ile Tyr Cys Th
                165                 170                 175

Ser Lys Asp Asp Gln Val Gly Ile Trp Ser Gly Pro Ala Pro Gln Cy
            180                 185                 190

Ile Ile Pro Asn Lys Cys
        195

(2) INFORMATION FOR SEQ ID NO: 37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

CAGTGCAACG TGCCGGAATG G                                                   21

(2) INFORMATION FOR SEQ ID NO: 38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

CCATTCCGGA ACGTTGCACT G                                                   21

(2) INFORMATION FOR SEQ ID NO: 39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

GACTGATGAT TTTGAGTTCC                                                     20

(2) INFORMATION FOR SEQ ID NO: 40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 40:

GGAACTCAAA ATCATCAGTC                                                         20

(2) INFORMATION FOR SEQ ID NO: 41:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 41:

GTCTGGACTA GTGCTAAGGA CAAGTGCAAA CGTAAATCTT GTCG                              44

(2) INFORMATION FOR SEQ ID NO: 42:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 42:

CGACAAGATT TACGTTTGCA CTTGTCCTTA GCACTAGTCC AGAC                              44

(2) INFORMATION FOR SEQ ID NO: 43:

(i) SEQUENCE CHARACTERISTICS:
            (A) LENGTH: 74 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 43:

CGGCATGGCG CATGTGATCA AAGATATCCA GTTCCGATCG CAAATTAAAT ATTCTTGTCC             60

TAAGGGTTAC CGTC                                                               74

(2) INFORMATION FOR SEQ ID NO: 44:

(i) SEQUENCE CHARACTERISTICS:
            (A) LENGTH: 74 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 44:

GACGGTAACC CTTAGGACAA GAATATTTAA TTTGCGATCG GAACTGGATA TCTTTGATCA             60

CATGCGCCAT GCCG                                                               74

(2) INFORMATION FOR SEQ ID NO: 45:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 45:

CATCTCTGGT AATACTGTCA TTTGGGATAA TAAAACACCG GTTTGTGACC        50

(2) INFORMATION FOR SEQ ID NO: 46:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 46:

GGTCACAAAC CGGTGTTTTA TTATCCCAAA TGACAGTATT ACCAGAGATG        50

(2) INFORMATION FOR SEQ ID NO: 47:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 47:

GACCGAATTA TCTGTGGTCT G                                      21

(2) INFORMATION FOR SEQ ID NO: 48:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 48:

CAGACCACAG ATAATTCGGT C                                      21

(2) INFORMATION FOR SEQ ID NO: 49:

(i) SEQUENCE CHARACTERISTICS:
      (A) LENGTH: 215 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 49:

Met Gln Cys Asn Val Pro Glu Trp Leu Pro Phe Ala Arg Pro Thr As
1               5                   10                  15

Leu Thr Asp Asp Phe Glu Phe Pro Ile Gly Thr Tyr Leu Asn Tyr Gl
            20                  25                  30

Cys Arg Pro Gly Tyr Ser Gly Arg Pro Phe Ser Ile Ile Cys Leu Ly
        35                  40                  45

Asn Ser Val Trp Thr Ser Ala Lys Asp Lys Cys Lys Arg Lys Ser Cy
    50                  55                  60

Arg Asn Pro Pro Asp Pro Val Asn Gly Met Ala His Val Ile Lys As
65                  70                  75                  80

```
Ile Gln Phe Arg Ser Gln Ile Lys Tyr Ser Cys Pro Lys Gly Tyr Ar
                85                  90                  95

Leu Ile Gly Ser Ser Ala Thr Cys Ile Ser Gly Asn Thr Va
            100                 105                 110

Ile Trp Asp Asn Lys Thr Pro Val Cys Asp Arg Ile Ile Cys Gly Le
            115                 120             125

Pro Pro Thr Ile Ala Asn Gly Asp Phe Thr Ser Ile Ser Arg Glu Ty
            130             135                 140

Phe His Tyr Gly Ser Val Val Thr Tyr His Cys Asn Leu Gly Ser Ar
145                 150                 155                 160

Gly Lys Lys Val Phe Glu Leu Val Gly Glu Pro Ser Ile Tyr Cys Th
                165                 170                 175

Ser Lys Asp Asp Gln Val Gly Ile Trp Ser Gly Pro Ala Pro Gln Cy
            180                 185                 190

Ile Ile Pro Asn Lys Cys Cys Asp Gly Pro Lys Lys Lys Lys Lys Ly
            195                 200                 205

Ser Pro Ser Lys Ser Ser Gly
210                 215
```

(2) INFORMATION FOR SEQ ID NO: 50:

(i) SEQUENCE CHARACTERISTICS:
        (A) LENGTH: 198 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 50:

```
Met Gln Cys Asn Val Pro Glu Trp Leu Pro Phe Ala Arg Pro Thr As
1               5                   10                  15

Leu Thr Asp Asp Phe Glu Phe Pro Ile Gly Thr Tyr Leu Asn Tyr Gl
            20                  25                  30

Cys Arg Pro Gly Tyr Ser Gly Arg Pro Phe Ser Ile Ile Cys Leu Ly
            35                  40                  45

Asn Ser Val Trp Thr Ser Ala Lys Asp Lys Cys Lys Arg Lys Ser Cy
50                  55                  60

Arg Asn Pro Pro Asp Pro Val Asn Gly Met Ala His Val Ile Lys As
65              70                  75                  80

Ile Gln Phe Arg Ser Gln Ile Lys Tyr Ser Cys Pro Lys Gly Tyr Ar
                85                  90                  95

Leu Ile Gly Ser Ser Ala Thr Cys Ile Ser Gly Asn Thr Va
            100                 105                 110

Ile Trp Asp Asn Lys Thr Pro Val Cys Asp Arg Ile Pro Cys Gly Le
            115                 120                 125

Pro Pro Thr Ile Ala Asn Gly Asp Phe Thr Ser Ile Ser Arg Glu Ty
            130             135                 140

Phe His Tyr Gly Ser Val Val Thr Tyr His Cys Asn Leu Gly Ser Ar
145                 150                 155                 160

Gly Lys Lys Val Phe Glu Leu Val Gly Glu Pro Ser Ile Tyr Cys Th
                165                 170                 175

Ser Lys Asp Asp Gln Val Gly Ile Trp Ser Gly Pro Ala Pro Gln Cy
            180                 185                 190

Ile Ile Pro Asn Lys Cys
            195
```

(2) INFORMATION FOR SEQ ID NO: 51:

(i) SEQUENCE CHARACTERISTICS:
        (A) LENGTH: 215 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 51:

```
Met Gln Cys Asn Val Pro Glu Trp Leu Pro Phe Ala Arg Pro Thr As
1               5                   10                  15

Leu Thr Asp Asp Phe Glu Phe Pro Ile Gly Thr Tyr Leu Asn Tyr Gl
            20                  25                  30

Cys Arg Pro Gly Tyr Ser Gly Arg Pro Phe Ser Ile Ile Cys Leu Ly
        35                  40                  45

Asn Ser Val Trp Thr Ser Ala Lys Asp Lys Cys Lys Arg Lys Ser Cy
50                  55                  60

Arg Asn Pro Pro Asp Pro Val Asn Gly Met Ala His Val Ile Lys As
65                  70                  75                  80

Ile Gln Phe Arg Ser Gln Ile Lys Tyr Ser Cys Pro Lys Gly Tyr Ar
            85                  90                  95

Leu Ile Gly Ser Ser Ala Thr Cys Ile Ile Ser Gly Asn Thr Va
            100                 105                 110

Ile Trp Asp Asn Lys Thr Pro Val Cys Asp Arg Ile Pro Cys Gly Le
            115                 120                 125

Pro Pro Thr Ile Ala Asn Gly Asp Phe Thr Ser Ile Ser Arg Glu Ty
130                 135                 140

Phe His Tyr Gly Ser Val Val Thr Tyr His Cys Asn Leu Gly Ser Ar
145                 150                 155                 160

Gly Lys Lys Val Phe Glu Leu Val Gly Glu Pro Ser Ile Tyr Cys Th
                165                 170                 175

Ser Lys Asp Asp Gln Val Gly Ile Trp Ser Gly Pro Ala Pro Gln Cy
            180                 185                 190

Ile Ile Pro Asn Lys Cys Cys Asp Gly Pro Lys Lys Lys Lys Lys Ly
            195                 200                 205

Ser Pro Ser Lys Ser Ser Gly
            210                 215
```

(2) INFORMATION FOR SEQ ID NO: 52:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 52:

CGCACCGCAG TGCATCATCC CGAACAAAGA TGGCCCGAGC GAAATTCTGC GTGGCGATTT        60

TAGCAGCTGC TA        72

(2) INFORMATION FOR SEQ ID NO: 53:

(i) SEQUENCE CHARACTERISTICS:
        (A) LENGTH: 80 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO: 53:

AGCTTAGCAG CTGCTAAAAT CGCCACGCAG AATTTCGCTC GGGCCATCTT TGTTCGGGAT    60

GATGCACTGC GGTGCGGGCC    80

(2) INFORMATION FOR SEQ ID NO: 54:

(i) SEQUENCE CHARACTERISTICS:
        (A) LENGTH: 211 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 54:

Met Gln Cys Asn Ala Pro Glu Trp Leu Pro Phe Ala Arg Pro Thr As
1               5                  10                 15

Leu Thr Asp Glu Phe Glu Phe Pro Ile Gly Thr Tyr Leu Asn Tyr Gl
            20                  25                  30

Cys Arg Pro Gly Tyr Ser Gly Arg Pro Phe Ser Ile Ile Cys Leu Ly
            35                  40                  45

Asn Ser Val Trp Thr Gly Ala Lys Asp Arg Cys Arg Arg Lys Ser Cy
        50                  55                  60

Arg Asn Pro Pro Asp Pro Val Asn Gly Met Val His Val Ile Lys Gl
65                  70                  75                  80

Ile Gln Phe Gly Ser Gln Ile Lys Tyr Ser Cys Thr Lys Gly Tyr Ar
                85                  90                  95

Leu Ile Gly Ser Ser Ser Ala Thr Cys Ile Ile Ser Gly Asp Thr Va
                100                 105                 110

Ile Trp Asp Asn Glu Thr Pro Ile Cys Asp Arg Ile Pro Cys Gly Le
        115                 120                 125

Pro Pro Thr Ile Ala Asn Gly Asp Phe Thr Ser Ile Ser Arg Glu Ty
    130                 135                 140

Phe His Tyr Gly Ser Val Val Thr Tyr His Cys Asn Leu Gly Ser Ar
145                 150                 155                 160

Gly Lys Lys Val Phe Glu Leu Val Gly Glu Pro Ser Ile Tyr Cys Th
                165                 170                 175

Ser Lys Asp Asp Gln Val Gly Ile Trp Ser Gly Pro Ala Pro Gln Cy
            180                 185                 190

Ile Ile Pro Asn Lys Asp Gly Pro Ser Glu Ile Leu Arg Gly Asp Ph
        195                 200                 205

Ser Ser Cys
    210

(2) INFORMATION FOR SEQ ID NO: 55:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 55:

```
CGCACCGCAG TGCATCATCC CGAACAAAGC GGCGCCCAGC GTGATTGGCT TCCGTATTCT      60

GCTGCTGAAA GTGGCGGGCT GATA                                           84
```

(2) INFORMATION FOR SEQ ID NO: 56:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 56:

```
AGCTTATCAG CCCGCCACTT TCAGCAGCAG AATACGGAAG CCAATCACGC TGGGCGCCGC      60

TTTGTTCGGG ATGATGCACT GCGGTGCGGG CC                                  92
```

(2) INFORMATION FOR SEQ ID NO: 57:

(i) SEQUENCE CHARACTERISTICS:
        (A) LENGTH: 214 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 57:

```
Met Gln Cys Asn Ala Pro Glu Trp Leu Pro Phe Ala Arg Pro Thr As
1               5                   10                  15

Leu Thr Asp Glu Phe Glu Phe Pro Ile Gly Thr Tyr Leu Asn Tyr Gl
                20                  25                  30

Cys Arg Pro Gly Tyr Ser Gly Arg Pro Phe Ser Ile Ile Cys Leu Ly
            35                  40                  45

Asn Ser Val Trp Thr Gly Ala Lys Asp Arg Cys Arg Arg Lys Ser Cy
        50                  55                  60

Arg Asn Pro Pro Asp Pro Val Asn Gly Met Val His Val Ile Lys Gl
65                  70                  75                  80

Ile Gln Phe Gly Ser Gln Ile Lys Tyr Ser Cys Thr Lys Gly Tyr Ar
                85                  90                  95

Leu Ile Gly Ser Ser Ser Ala Thr Cys Ile Ile Ser Gly Asp Thr Va
                100                 105                 110

Ile Trp Asp Asn Glu Thr Pro Ile Cys Asp Arg Ile Pro Cys Gly Le
            115                 120                 125

Pro Pro Thr Ile Ala Asn Gly Asp Phe Thr Ser Ile Ser Arg Glu Ty
    130                 135                 140

Phe His Tyr Gly Ser Val Val Thr Tyr His Cys Asn Leu Gly Ser Ar
145                 150                 155                 160

Gly Lys Lys Val Phe Glu Leu Val Gly Glu Pro Ser Ile Tyr Cys Th
                165                 170                 175

Ser Lys Asp Asp Gln Val Gly Ile Trp Ser Gly Pro Ala Pro Gln Cy
            180                 185                 190

Ile Ile Pro Asn Lys Ala Ala Pro Ser Val Ile Gly Phe Arg Ile Le
        195                 200                 205

Leu Leu Lys Val Ala Gly
    210
```

(2) INFORMATION FOR SEQ ID NO: 58:

(i) SEQUENCE CHARACTERISTICS:
        (A) LENGTH: 438 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 58:

```
Gln Cys Asn Val Pro Glu Trp Leu Pro Phe Ala Arg Pro Thr Asn Le
1               5                   10                  15

Thr Asp Asp Phe Glu Phe Pro Ile Gly Thr Tyr Leu Asn Tyr Glu Cy
            20                  25                  30

Arg Pro Gly Tyr Ser Gly Arg Pro Phe Ser Ile Ile Cys Leu Lys As
            35                  40                  45

Ser Val Trp Thr Ser Ala Lys Asp Lys Cys Lys Arg Lys Ser Cys Ar
        50                  55                  60

Asn Pro Pro Asp Pro Val Asn Gly Met Ala His Val Ile Lys Asp Il
65                  70                  75                  80

Gln Phe Arg Ser Gln Ile Lys Tyr Ser Cys Pro Lys Gly Tyr Arg Le
                85                  90                  95

Ile Gly Ser Ser Ser Ala Thr Cys Ile Ile Ser Gly Asn Thr Val Il
                100                 105                 110

Trp Asp Asn Lys Thr Pro Val Cys Asp Arg Ile Ile Cys Gly Leu Pr
                115                 120                 125

Pro Thr Ile Ala Asn Gly Asp Phe Thr Ser Ile Ser Arg Glu Tyr Ph
        130                 135                 140

His Tyr Gly Ser Val Val Thr Tyr His Cys Asn Leu Gly Ser Arg Gl
145                 150                 155                 160

Lys Lys Val Phe Glu Leu Val Gly Glu Pro Ser Ile Tyr Cys Thr Se
                165                 170                 175

Lys Asp Asp Gln Val Gly Ile Trp Ser Gly Pro Ala Pro Gln Cys Il
                180                 185                 190

Ile Pro Asn Lys Cys Thr Pro Pro Asn Val Glu Asn Gly Ile Leu Va
                195                 200                 205

Ser Asp Asn Arg Ser Leu Phe Ser Leu Asn Glu Val Val Glu Phe Ar
        210                 215                 220

Cys Gln Pro Gly Phe Gly Met Lys Gly Pro Ser His Val Lys Cys Gl
225                 230                 235                 240

Ala Leu Asn Lys Trp Glu Pro Glu Leu Pro Ser Cys Ser Arg Val Cy
                245                 250                 255

Gln Pro Pro Pro Asp Val Leu His Ala Glu Arg Thr Gln Arg Asp Ly
                260                 265                 270

Asp Asn Phe Ser Pro Gly Gln Glu Val Phe Tyr Ser Cys Glu Pro Gl
        275                 280                 285

Tyr Asp Leu Arg Gly Ser Thr Tyr Leu His Cys Thr Pro Gln Gly As
        290                 295                 300

Trp Ser Pro Ala Ala Pro Arg Cys Glu Val Lys Ser Cys Asp Asp Ph
305                 310                 315                 320

Leu Gly Gln Leu Pro Asn Gly His Val Leu Phe Pro Leu Asn Leu Gl
                325                 330                 335

Leu Gly Ala Lys Val Asp Phe Val Cys Asp Glu Gly Phe Gln Leu Ly
                340                 345                 350

Gly Ser Ser Ala Ser Tyr Cys Val Leu Ala Gly Met Glu Ser Leu Tr
                355                 360                 365
```

```
Asn Ser Ser Val Pro Val Cys Glu Arg Glu Ser Cys Lys Thr Pro Pr
    370                 375                 380
Val Pro Val Asn Gly Met Val His Val Ile Thr Asp Ile His Val Gl
385                 390                 395                 400
Ser Arg Ile Asn Tyr Ser Cys Thr Thr Gly His Arg Leu Ile Gly Hi
            405                 410                 415
Ser Ser Ala Glu Cys Ile Leu Ser Gly Asn Thr Ala His Trp Ser Me
        420                 425                 430
Lys Pro Pro Ile Cys Gln
        435
```

(2) INFORMATION FOR SEQ ID NO: 59:

(i) SEQUENCE CHARACTERISTICS:
        (A) LENGTH: 477 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 59:

```
Val Gly Pro Pro Ala Pro Gly Leu Pro Phe Cys Cys Gly Gly Ser Le
1                 5                  10                  15
Leu Ala Val Val Val Leu Leu Ala Leu Pro Val Ala Trp Gly Gln Cy
            20                  25                  30
Asn Ala Pro Glu Trp Leu Pro Phe Ala Arg Pro Thr Asn Leu Thr As
        35                  40                  45
Glu Phe Glu Phe Pro Ile Gly Thr Tyr Leu Asn Tyr Glu Cys Arg Pr
50                  55                  60
Gly Tyr Ser Gly Arg Pro Phe Ser Ile Ile Cys Leu Lys Asn Ser Va
65                  70                  75                  80
Trp Thr Gly Ala Lys Asp Arg Cys Arg Arg Lys Ser Cys Arg Asn Pr
            85                  90                  95
Pro Asp Pro Val Asn Gly Met Val His Val Ile Lys Gly Ile Gln Ph
        100                 105                 110
Gly Ser Gln Ile Lys Tyr Ser Cys Thr Lys Gly Tyr Arg Leu Ile Gl
            115                 120                 125
Ser Ser Ala Thr Cys Ile Ile Ser Gly Asp Thr Val Ile Trp As
    130                 135                 140
Asn Glu Thr Pro Ile Cys Asp Arg Ile Pro Cys Gly Leu Pro Pro Th
145                 150                 155                 160
Ile Thr Asn Gly Asp Phe Ile Ser Thr Asn Arg Glu Asn Phe His Ty
            165                 170                 175
Gly Ser Val Val Thr Tyr Arg Cys Asn Pro Gly Ser Gly Gly Arg Ly
        180                 185                 190
Val Phe Glu Leu Val Gly Glu Pro Ser Ile Tyr Cys Thr Ser Asn As
        195                 200                 205
Asp Gln Val Gly Ile Trp Ser Gly Pro Ala Pro Gln Cys Ile Ile Pr
    210                 215                 220
Asn Lys Cys Thr Pro Pro Asn Val Glu Asn Gly Ile Leu Val Ser As
225                 230                 235                 240
Asn Arg Ser Leu Phe Ser Leu Asn Glu Val Val Glu Phe Arg Cys Gl
            245                 250                 255
Pro Gly Phe Val Met Lys Gly Pro Arg Arg Val Lys Cys Gln Ala Le
        260                 265                 270
```

```
Asn Lys Trp Glu Pro Glu Leu Pro Ser Cys Ser Arg Val Cys Gln Pr
        275                 280                 285

Pro Pro Asp Val Leu His Ala Glu Arg Thr Gln Arg Asp Lys Asp As
        290                 295                 300

Phe Ser Pro Gly Gln Glu Val Phe Tyr Ser Cys Glu Pro Gly Tyr As
305                 310                 315                 320

Leu Arg Gly Ala Ala Ser Met Arg Cys Thr Pro Gln Gly Asp Trp Se
                325                 330                 335

Pro Ala Ala Pro Thr Cys Glu Val Lys Ser Cys Asp Asp Phe Met Gl
                340                 345                 350

Gln Leu Leu Asn Gly Arg Val Leu Phe Pro Val Asn Leu Gln Leu Gl
            355                 360                 365

Ala Lys Val Asp Phe Val Cys Asp Glu Gly Phe Gln Leu Lys Gly Se
        370                 375                 380

Ser Ala Ser Tyr Cys Val Leu Ala Gly Met Glu Ser Leu Trp Asn Se
385                 390                 395                 400

Ser Val Pro Val Cys Glu Gln Ile Phe Cys Pro Ser Pro Val Il
                405                 410                 415

Pro Asn Gly Arg His Thr Gly Lys Pro Leu Glu Val Phe Pro Phe Gl
                420                 425                 430

Lys Ala Val Asn Tyr Thr Cys Asp Pro His Pro Asp Arg Gly Thr Se
                435                 440                 445

Phe Asp Leu Ile Gly Glu Ser Thr Ile Arg Cys Thr Ser Asp Pro Gl
                450                 455                 460

Gly Asn Gly Val Trp Ser Pro Ala Pro Arg Cys Gly
465                 470                 475

(2) INFORMATION FOR SEQ ID NO: 60:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 60:

Asp Gly Pro Lys Lys Lys Lys Lys Ser Pro Ser Lys Ser Ser Gl
1               5                   10                  15

(2) INFORMATION FOR SEQ ID NO: 61:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 61:

Gly Ser Ser Lys Ser Pro Ser Lys Lys Lys Lys Lys Pro Gly As
1               5                   10                  15

(2) INFORMATION FOR SEQ ID NO: 62:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear
```

(ii) MOLECULE TYPE: peptide (xi) SEQUENCE DESCRIPTION: SEQ ID NO: 62:

```
Ser Asn Ser Asn Glu Thr Pro Lys Lys Lys Lys Arg Phe Ser Ph
1               5                  10                  15
Lys Lys Ser Gly
            20
```

(2) INFORMATION FOR SEQ ID NO: 63:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 63:

```
Gly Arg Gly Asp Ser Pro
1               5
```

(2) INFORMATION FOR SEQ ID NO: 64:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 64:

```
Gly Asn Glu Gln Ser Phe Arg Val Asp Leu Arg Thr Leu Leu Arg Ty
1               5                  10                  15
Ala
```